US011020592B2

(12) United States Patent
Tyulmankov et al.

(10) Patent No.: US 11,020,592 B2
(45) Date of Patent: Jun. 1, 2021

(54) SYSTEMS AND METHODS FOR GENERATING INTERMITTENT STIMULATION USING ELECTRICAL STIMULATION SYSTEMS

(71) Applicant: Boston Scientific Neuromodulation Corporation, Valencia, CA (US)

(72) Inventors: Danil Tyulmankov, Cambridge, MA (US); Hemant Bokil, Santa Monica, CA (US); Peter Alexander Tass, Palo Alto, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 216 days.

(21) Appl. No.: 16/193,969

(22) Filed: Nov. 16, 2018

(65) Prior Publication Data

US 2019/0151657 A1 May 23, 2019

Related U.S. Application Data

(60) Provisional application No. 62/588,173, filed on Nov. 17, 2017.

(51) Int. Cl.
*A61N 1/36* (2006.01)
*A61N 1/02* (2006.01)
(Continued)

(52) U.S. Cl.
CPC .......... *A61N 1/3603* (2017.08); *A61N 1/025* (2013.01); *A61N 1/0404* (2013.01);
(Continued)

(58) Field of Classification Search
CPC ... A61N 1/18; A61N 1/32; A61N 1/36; A61N 1/3603; A61N 1/36034; A61N 1/3605;
(Continued)

(56) References Cited

U.S. PATENT DOCUMENTS

| 4,813,418 A | 3/1989 | Harris |
| 6,067,474 A | 5/2000 | Schulman et al. |

(Continued)

FOREIGN PATENT DOCUMENTS

| DE | 10318071 A1 | 11/2004 |
| WO | 02/09808 A1 | 2/2002 |

(Continued)

OTHER PUBLICATIONS

Larson, J. et al., "Reversal of LTP by theta frequency stimulation", Brain Research, Elsevier, Amsterdam, NL, vol. 600 No. 1, Jan. 8, 1993, pp. 97-102.

(Continued)

*Primary Examiner* — Allen Porter
(74) *Attorney, Agent, or Firm* — Branch Partners PLLC; Bruce E. Black

(57) ABSTRACT

A system for providing electrical stimulation to a patient includes a processor configured to: provide a time-ordered arrangement of multiple stimulation instances, where each of the stimulation instances is configured to produce a different stimulation field from each other stimulation instance in the arrangement; provide an ON/OFF switch pattern that includes alternating ON periods and OFF periods; generate an intermittent stimulation program that corresponds to repetition of the arrangement of stimulation instances with omission of each of the stimulation instances occurring during the OFF periods; and initiate a signal that provides a pulse generator with instructions that enable the pulse generator to generate stimulation according to the intermittent stimulation program using an electrical stimulation lead coupled to the pulse generator.

18 Claims, 10 Drawing Sheets

(51) Int. Cl.
  *A61N 1/04* (2006.01)
  *A61N 1/05* (2006.01)
  *A61N 1/08* (2006.01)
  *G16H 20/40* (2018.01)

(52) U.S. Cl.
  CPC .............. *A61N 1/0551* (2013.01); *A61N 1/08* (2013.01); *A61N 1/36067* (2013.01); *A61N 1/36082* (2013.01); *A61N 1/36171* (2013.01); *A61N 1/36178* (2013.01); *G16H 20/40* (2018.01)

(58) Field of Classification Search
  CPC ............ A61N 1/36062; A61N 1/36128; A61N 1/36135; A61N 1/36139; A61N 1/36146; A61N 1/36167
  See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 7,244,150 B1 | 7/2007 | Brase et al. |
| 7,346,282 B2 | 3/2008 | Sakanaka et al. |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,761,165 B1 | 7/2010 | He et al. |
| 7,783,359 B2 | 8/2010 | Meadows |
| 7,792,590 B1 | 9/2010 | Pianca et al. |
| 7,809,446 B2 | 10/2010 | Meadows |
| 7,917,221 B2 | 3/2011 | Tass |
| 7,949,395 B2 | 5/2011 | Kuzma |
| 7,974,698 B2 | 7/2011 | Tass et al. |
| 7,974,706 B2 | 7/2011 | Moffitt et al. |
| 8,000,794 B2 | 8/2011 | Lozano |
| 8,000,795 B2 | 8/2011 | Lozano |
| 8,000,796 B2 | 8/2011 | Tass et al. |
| 8,078,275 B2 | 12/2011 | Lozano |
| 8,116,874 B2 | 2/2012 | Tass |
| 8,175,710 B2 | 5/2012 | He |
| 8,180,601 B2 | 5/2012 | Butson et al. |
| 8,209,027 B2 | 6/2012 | Butson et al. |
| 8,224,450 B2 | 7/2012 | Brase |
| 8,271,094 B1 | 9/2012 | Moffitt et al. |
| 8,280,514 B2 | 10/2012 | Lozano et al. |
| 8,295,944 B2 | 10/2012 | Howard et al. |
| 8,326,433 B2 | 12/2012 | Blum et al. |
| 8,346,365 B2 | 1/2013 | Lozano |
| 8,364,278 B2 | 1/2013 | Pianca et al. |
| 8,380,304 B2 | 2/2013 | Lozano |
| 8,391,985 B2 | 3/2013 | McDonald |
| 8,463,378 B2 | 6/2013 | Tass |
| 8,463,386 B2 | 6/2013 | Tass |
| 8,473,059 B2 | 6/2013 | Tass et al. |
| 8,473,061 B2 | 6/2013 | Moffitt et al. |
| 8,538,547 B2 | 9/2013 | Tass et al. |
| 8,565,883 B2 | 10/2013 | Lozano |
| 8,571,665 B2 | 10/2013 | Moffitt et al. |
| 8,589,316 B2 | 11/2013 | Lujan et al. |
| 8,594,800 B2 | 11/2013 | Butson et al. |
| 8,606,360 B2 | 12/2013 | Butson et al. |
| 8,612,006 B2 | 12/2013 | Lozano et al. |
| 8,675,945 B2 | 3/2014 | Barnhorst et al. |
| 8,688,235 B1 | 4/2014 | Pianca et al. |
| 8,721,695 B2 | 5/2014 | Tass et al. |
| 8,792,993 B2 | 7/2014 | Pianca et al. |
| 8,831,731 B2 | 9/2014 | Blum et al. |
| 8,849,632 B2 | 9/2014 | Sparks et al. |
| 8,868,191 B2 | 10/2014 | Lozano |
| 8,914,115 B2 | 12/2014 | Giftakis et al. |
| 8,958,615 B2 | 2/2015 | Blum et al. |
| 9,020,789 B2 | 4/2015 | Butson et al. |
| 9,050,470 B2 | 6/2015 | Carlton et al. |
| 9,072,905 B2 | 7/2015 | Kokones et al. |
| 9,227,066 B2 | 1/2016 | Lozano |
| 9,327,124 B2 | 5/2016 | Tass |
| 9,486,389 B2 | 11/2016 | Tass |
| 9,826,916 B2 | 11/2017 | Tass |
| 2003/0191506 A1 | 10/2003 | Shloznikov |
| 2004/0210271 A1 | 10/2004 | Campen |
| 2005/0075696 A1 | 4/2005 | Forsberg et al. |
| 2005/0125043 A1 | 6/2005 | Tass |
| 2005/0154424 A1 | 7/2005 | Tass et al. |
| 2005/0216071 A1 | 9/2005 | Delvin et al. |
| 2006/0015153 A1 | 1/2006 | Bradford et al. |
| 2006/0212090 A1 | 9/2006 | Lozano et al. |
| 2007/0100377 A1* | 5/2007 | Armstrong ......... A61N 1/36146 607/2 |
| 2007/0135860 A1 | 6/2007 | Tass |
| 2007/0142874 A1 | 6/2007 | John |
| 2007/0150036 A1 | 6/2007 | Anderson |
| 2007/0225674 A1 | 9/2007 | Molnar et al. |
| 2008/0071325 A1 | 3/2008 | Bradley |
| 2008/0215113 A1 | 9/2008 | Pawlowicz |
| 2009/0082829 A1 | 3/2009 | Panken et al. |
| 2009/0083070 A1 | 3/2009 | Giftakis et al. |
| 2009/0112281 A1 | 4/2009 | Miyazawa et al. |
| 2009/0132010 A1* | 5/2009 | Kronberg ................. A61N 1/32 607/72 |
| 2009/0187222 A1 | 7/2009 | Barker |
| 2009/0276021 A1 | 11/2009 | Meadows et al. |
| 2009/0281594 A1 | 11/2009 | King et al. |
| 2009/0287272 A1 | 11/2009 | Kokones et al. |
| 2009/0287273 A1 | 11/2009 | Carlton et al. |
| 2010/0076535 A1 | 5/2010 | Pianca et al. |
| 2010/0121416 A1* | 5/2010 | Lee ..................... A61N 1/36146 607/66 |
| 2010/0268298 A1 | 10/2010 | Pianca et al. |
| 2010/0280570 A1 | 11/2010 | Sturm et al. |
| 2011/0004267 A1 | 1/2011 | Meadows et al. |
| 2011/0005069 A1 | 1/2011 | Pianca |
| 2011/0077720 A1 | 3/2011 | Torgerson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0201977 A1 | 8/2011 | Tass |
| 2011/0238129 A1 | 9/2011 | Moffitt et al. |
| 2011/0251583 A1 | 10/2011 | Miyazawa et al. |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0274273 A1 | 11/2012 | Jacobs et al. |
| 2012/0314924 A1 | 12/2012 | Carlton et al. |
| 2012/0316615 A1 | 12/2012 | DiGiore et al. |
| 2013/0066394 A1 | 3/2013 | Saab |
| 2013/0090519 A1* | 4/2013 | Tass ..................... A61M 21/00 600/28 |
| 2013/0105071 A1 | 5/2013 | DiGiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0218239 A1 | 8/2013 | Grill et al. |
| 2013/0231713 A1 | 9/2013 | De Ridder |
| 2013/0289385 A1 | 10/2013 | Lozano et al. |
| 2013/0317583 A1 | 11/2013 | Pianca |
| 2013/0317585 A1 | 11/2013 | Barker |
| 2013/0317586 A1 | 11/2013 | Pianca |
| 2013/0317587 A1 | 11/2013 | Barker |
| 2013/0317588 A1 | 11/2013 | Howard et al. |
| 2014/0025133 A1 | 1/2014 | Lozano |

(56) References Cited

U.S. PATENT DOCUMENTS

| | | |
|---|---|---|
| 2014/0039587 A1 | 2/2014 | Romero |
| 2014/0081349 A1 | 3/2014 | Lee et al. |
| 2014/0122379 A1 | 5/2014 | Moffitt et al. |
| 2014/0277250 A1 | 9/2014 | Su et al. |
| 2014/0277281 A1 | 9/2014 | Grandhe |
| 2014/0277284 A1 | 9/2014 | Chen et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0018915 A1 | 1/2015 | Leven |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2016/0030666 A1 | 2/2016 | Lozano et al. |
| 2016/0030749 A1 | 2/2016 | Carcieri et al. |
| 2016/0121126 A1 | 5/2016 | Marnfeldt |
| 2016/0228692 A1 | 8/2016 | Steinke et al. |
| 2017/0259068 A1 | 9/2017 | Tass et al. |
| 2017/0296823 A1 | 10/2017 | Hershey et al. |
| 2017/0333711 A1 | 11/2017 | Tess et al. |
| 2018/0178014 A1 | 6/2018 | Tass et al. |
| 2018/0280697 A1 | 10/2018 | Tass et al. |
| 2019/0001140 A1 | 1/2019 | Tass et al. |

FOREIGN PATENT DOCUMENTS

| | | |
|---|---|---|
| WO | 2009/021481 | 2/2009 |
| WO | 2009/055127 A1 | 4/2009 |
| WO | 2010/112023 | 10/2010 |
| WO | 2011/127917 | 10/2011 |

OTHER PUBLICATIONS

Borys Lysyansky et al: Desynchronizing anti-resonance effect of m:n. On-Off coordinated reset stimulation; Journal of Neural Engineering, Institute of Physics Publishing, Bristol, GB, vol. 8, No. 3, May 10, 2011 (May 10, 2011), 13 pages.

International Search Report and Written Opinion for PCT Application No. PCT/US2018/061599 dated Feb. 14, 2019.

\* cited by examiner

SYSTEMS AND METHODS FOR GENERATING INTERMITTENT STIMULATION USING ELECTRICAL STIMULATION SYSTEMS

CROSS-REFERENCE TO RELATED APPLICATIONS

This application claims the benefit under 35 U.S.C. § 119(e) of U.S. Provisional Patent Application Ser. No. 62/588,173, filed Nov. 17, 2017, which is incorporated herein by reference.

FIELD

The present invention is directed to the area of electrical stimulation systems and methods of making and using the systems. The present invention is also directed to systems and methods for generating and applying intermittent electrical stimulation to a patient using implantable electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include an implantable pulse generator ("IPG"), one or more leads, and an array of stimulator electrodes on each lead. The stimulator electrodes are in contact with or near the nerves, muscles, or other tissue to be stimulated. The pulse generator generates electrical pulses that are delivered by the electrodes to body tissue.

BRIEF SUMMARY

In one embodiment, a system for providing electrical stimulation to a patient includes a processor configured to: provide a time-ordered arrangement of multiple stimulation instances, where each of the stimulation instances in the arrangement has a corresponding set of stimulation parameters, including a stimulation duration, and is configured to produce a different stimulation field from each other stimulation instance in the arrangement; provide an ON/OFF switch pattern that includes alternating ON periods and OFF periods, where at least one of the ON periods or one of the OFF periods is longer than a combined stimulation duration of two consecutive ones of the stimulation instances; generate an intermittent stimulation program that is a repetition of the arrangement of stimulation instances with omission of each of the stimulation instances occurring during the OFF periods; and initiate a signal that provides a pulse generator with instructions that enable the pulse generator to generate stimulation according to the intermittent stimulation program using an electrical stimulation lead coupled to the pulse generator.

In at least some embodiments, the system further includes a pulse generator in communication with the processor. The pulse generator is configured to generate stimulation according to the intermittent stimulation program. An electrical stimulation lead is coupleable to the pulse generator. The electrical stimulation lead includes electrodes configured to stimulate patient tissue when coupled to the pulse generator. In at least some embodiments, the set of stimulation parameters for each stimulation instance of the intermittent stimulation program includes a selection of an individual electrode or a subset of electrodes from the electrodes. In at least some embodiments, the arrangement of stimulation instances has a time duration corresponding to a frequency within a pathological frequency range associated with a neuronal population at a target stimulation location in proximity to the plurality of electrodes.

In at least some embodiments, the stimulation instances include a first stimulation instance and a second stimulation instance, where the ON/OFF-switch pattern includes a first ON/OFF-switch sub-pattern applicable only to the first stimulation instance, and where the intermittent stimulation program includes repetition of the arrangement of stimulation instances with omission of each of the first stimulation instances occurring during the OFF periods of the first ON/OFF-switch sub-pattern. In at least some embodiments, the ON/OFF-switch pattern includes a second ON/OFF-switch sub-pattern, the second ON/OFF-switch sub-pattern applicable only to the second stimulation instance, and where the intermittent stimulation program includes repetition of the arrangement of stimulation instances with omission of each of the second stimulation instances occurring during the OFF periods of the second ON/OFF-switch sub-pattern.

In at least some embodiments, the ON periods of the ON/OFF-switch pattern have equal duration to the OFF periods. In at least some embodiments, the ON periods of the ON/OFF-switch pattern have unequal duration to OFF periods. In at least some embodiments, the ON periods of the ON/OFF-switch pattern are of uniform duration. In at least some embodiments, the ON periods of the ON/OFF-switch pattern are of non-uniform duration. In at least some embodiments, the OFF periods of the ON/OFF-switch pattern are of uniform duration. In at least some embodiments, the OFF periods of the ON/OFF-switch pattern are of non-uniform duration. In at least some embodiments, the ON periods and the OFF periods of the ON/OFF-switch pattern are of randomly-determined durations. In at least some embodiments, each of the stimulation instances occurs exactly once in the arrangement and in a predetermined order in time In another embodiment, a method for providing intermittent electrical stimulation to a patient includes advancing an electrical stimulation lead to a target stimulation location within the patient. The electrical stimulation lead includes electrodes. The electrical stimulation lead is coupled to a pulse generator configured for providing electrical stimulation signals to the electrodes for stimulation of patient tissue. The above-described system is used for initiating signals that provide the pulse generator with instructions that enable the pulse generator to generate stimulation according to the intermittent pattern of stimulations of the system using the electrical stimulation lead. In at least some embodiments, the repeating arrangements of stimulation instances of the system are programmed to have a time duration corresponding to a frequency within a pathological frequency range associated with a neuronal population at a target stimulation location in proximity to the plurality of electrodes.

In yet another embodiment, a non-transitory computer-readable medium has processor-executable instructions for programming electrical stimulation by an electrical stimulation lead. The processor-executable instructions, when installed onto a device, enable the device to perform actions, including providing a time-ordered arrangement of stimulation instances, where each of the stimulation instances in the arrangement has a corresponding set of stimulation parameters, including a stimulation duration, and is configured to produce a different stimulation field from each other stimulation instance in the arrangement. An ON/OFF switch pattern is provided that includes alternating ON periods and OFF periods. At least one of the ON periods or one of the OFF periods is longer than a combined stimulation duration of two consecutive ones of the stimulation instances. An intermittent stimulation program is generated that is a repetition of the arrangement of stimulation instances with omission of each of the stimulation instances occurring during the OFF periods. A signal is initiated that provides a pulse generator with instructions that enable the pulse generator to generate stimulation according to the intermittent stimulation program using an electrical stimulation lead coupled to the pulse generator.

In still yet another embodiment, a system for providing electrical stimulation to a patient includes a processor configured to: provide a time-ordered arrangement of multiple stimulation instances, where each of the stimulation instances in the arrangement has a corresponding set of stimulation parameters, including a stimulation duration, and is configured to produce a different stimulation field from each other stimulation instance in the arrangement, and where each of the stimulation instances occurs in a non-uniform order in time; provide an ON/OFF switch pattern that includes alternating ON periods and OFF periods, where at least one of the ON periods or one of the OFF periods is longer than a combined stimulation duration of two consecutive ones of the stimulation instances; generate an intermittent stimulation program that is a repetition of the arrangement of stimulation instances with omission of each of the stimulation instances occurring during the OFF periods; and initiate a signal that provides a pulse generator with instructions that enable the pulse generator to generate stimulation according to the intermittent stimulation program using an electrical stimulation lead coupled to the pulse generator. In at least some embodiments, each of the stimulation instances occurs exactly once in the arrangement and in a randomly-determined order in time.

In another embodiment, a method for providing intermittent electrical stimulation to a patient includes advancing an electrical stimulation lead to a target stimulation location within the patient. The electrical stimulation lead includes electrodes. The electrical stimulation lead is coupled to a pulse generator configured for providing electrical stimulation signals to the electrodes for stimulation of patient tissue. The above-described system is used for initiating signals that provide the pulse generator with instructions that enable the pulse generator to generate stimulation according to the intermittent pattern of stimulations of the system using the electrical stimulation lead. In at least some embodiments, repeating arrangements of stimulation instances of the system are programmed to have a time duration corresponding to a frequency within a pathological frequency range associated with a neuronal population at a target stimulation location in proximity to the plurality of electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of electrical stimulation systems and methods of making and using the systems. The present invention is also directed to systems and methods for generating and applying intermittent electrical stimulation to a patient using implantable electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, cuff leads, or any other arrangement of electrodes on a lead. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Applications Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference. In the discussion below, a percutaneous lead will be exemplified, but it will be understood that the methods and systems described herein are also applicable to paddle leads and other leads.

A percutaneous lead for electrical stimulation (for example, deep brain, spinal cord, peripheral nerve, or cardiac-tissue stimulation) includes stimulation electrodes that can be ring electrodes, segmented electrodes that extend only partially around the circumference of the lead, or any other type of electrode, or any combination thereof. The segmented electrodes can be provided in sets of electrodes, with each set having electrodes circumferentially distributed about the lead at a particular longitudinal position. A set of segmented electrodes can include any suitable number of electrodes including, for example, two, three, four, or more electrodes. For illustrative purposes, the leads are described herein relative to use for deep brain stimulation, but it will be understood that any of the leads can be used for applications other than deep brain stimulation, including spinal cord stimulation, peripheral nerve stimulation, dorsal root ganglion stimulation, sacral nerve stimulation, or stimulation of other nerves, muscles, and tissues.

Figure 1:
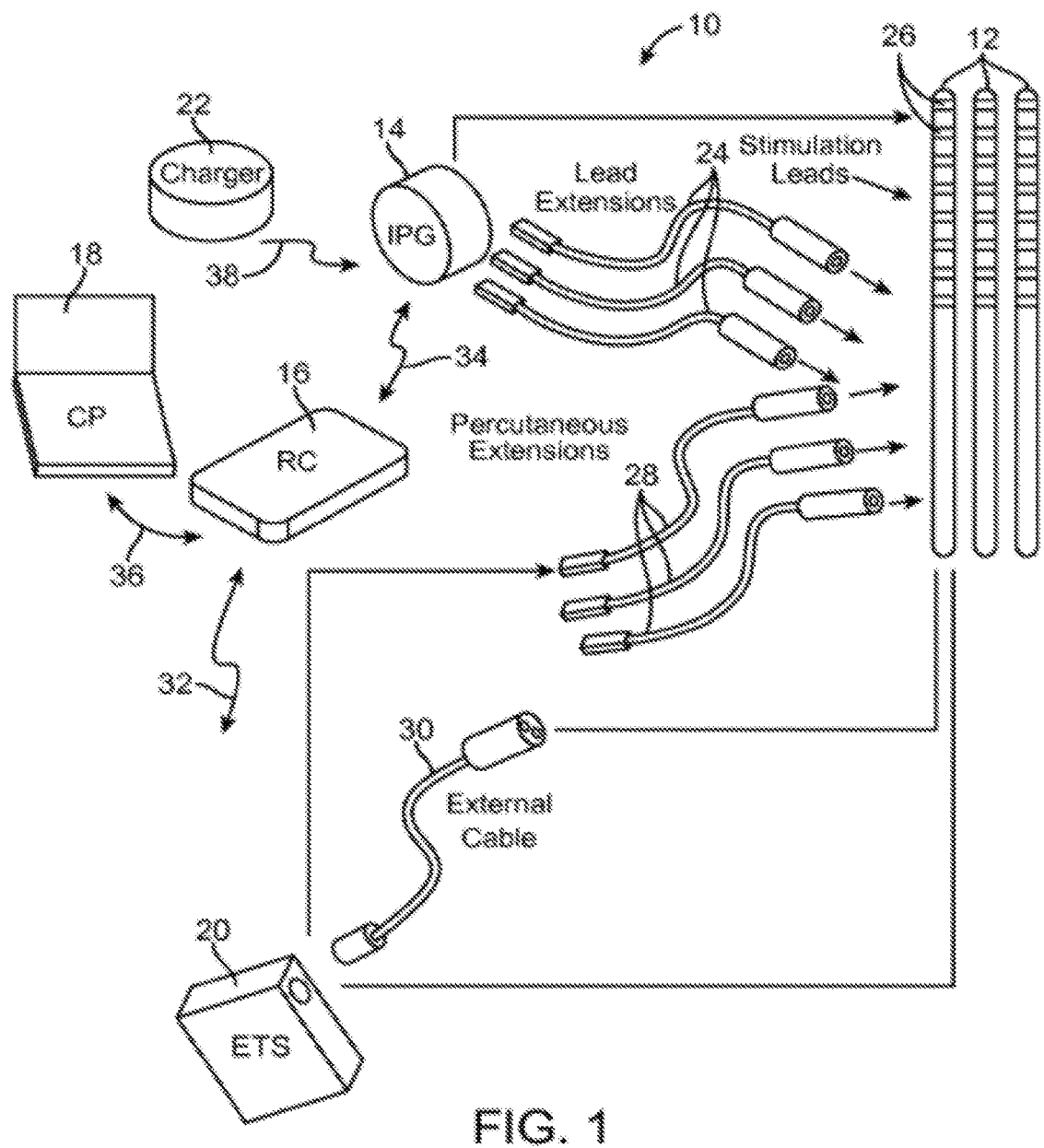
FIG. 1 is a schematic view of one embodiment of an electrical stimulation system, according to the invention.

Turning to FIG. 1, one embodiment of an electrical stimulation system 10 includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The implantable pulse generator can be implanted into a patient's body, for example, below the patient's clavicle area or within the patient's buttocks or abdominal cavity. The implantable pulse generator can have eight stimulation channels which may be independently programmable to control the magnitude of the current stimulus from each channel. In some embodiments, the implantable pulse generator can have more or fewer than eight stimulation channels (e.g., 4-, 6-, 16-, 32-, or more stimulation channels). The implantable pulse generator can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. Alternately, or additionally, stimulation parameters can be programed via wireless communications (e.g., Bluetooth) between the RC 16 (or external device such as a hand-held electronic device) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

For purposes of brevity, the details of the RC 16, CP 18, ETS 20, and external charger 22 will not be further described herein. Details of exemplary embodiments of these devices are disclosed in U.S. Pat. No. 6,895,280, which is expressly incorporated herein by reference. Other examples of electrical stimulation systems can be found at U.S. Pat. Nos. 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, as well as the other references cited above, all of which are incorporated by reference.

Figure 2:
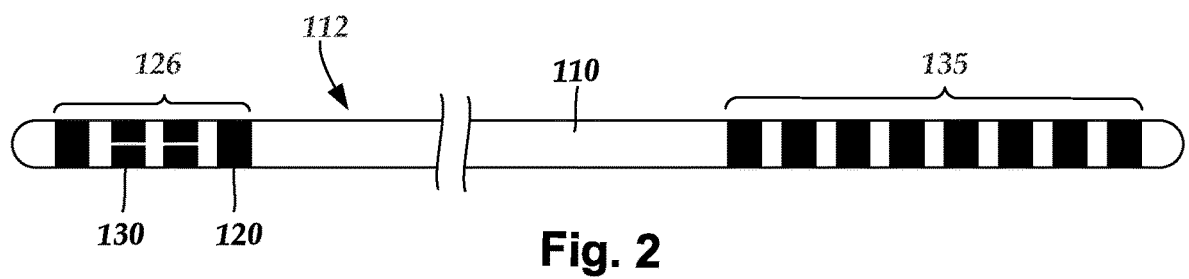
FIG. 2 is a schematic side view of one embodiment of an electrical stimulation lead, according to the invention.

FIG. 2 illustrates one embodiment of a lead 112 with electrodes 126 disposed at least partially about a circumference of the lead 112 along a distal end portion of the lead and terminals 135 disposed along a proximal end portion of the lead. The lead 112 can be implanted near or within the desired portion of the body to be stimulated such as, for example, the brain, spinal cord, or other body organs or tissues. In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 112 can be inserted into the cranium and brain tissue with the assistance of a stylet (not shown). The lead 112 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 112, advance the lead 112, retract the lead 112, or rotate the lead 112.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 112 for deep brain stimulation can include stimulation electrodes, recording electrodes, or both. In at least some embodiments, the lead 112 is rotatable so that the stimulation electrodes can be aligned with the target neurons after the neurons have been located using the recording electrodes.

Stimulation electrodes may be disposed on the circumference of the lead 112 to stimulate the target neurons. Stimulation electrodes may be ring-shaped so that current projects from each electrode equally in every direction from the position of the electrode along a length of the lead 112. In the embodiment of FIG. 2, two of the electrodes 126 are ring electrodes 120. Ring electrodes typically do not enable stimulus current to be directed from only a limited angular range around of the lead. Segmented electrodes 130, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead). To achieve current steering, segmented electrodes can be utilized in addition to, or as an alternative to, ring electrodes.

The lead 112 includes a lead body 110, terminals 135, and one or more ring electrodes 120 and one or more sets of segmented electrodes 130 (or any other combination of electrodes). The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 112 has a cross-sectional diameter of no more than 1.5 mm and may be in the range of 0.5 to 1.5 mm. In at least some embodiments, the lead 100 has a length of at least 10 cm and the length of the lead 112 may be in the range of 10 to 70 cm.

The electrodes 126 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Pat. Nos. 8,473,061; 8,571,665; and 8,792,993; U.S. Patent Application Publications Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/0197375; 2012/0203316; 2012/0203320; 2012/0203321; 2013/0197424; 2013/0197602; 2014/0039587; 2014/0353001; 2014/0358208; 2014/0358209; 2014/0358210; 2015/0045864; 2015/0066120; 2015/0018915; 2015/0051681; U.S. patent application Ser. Nos. 14/557,211 and 14/286,797; and U.S. Provisional Patent Application Ser. No. 62/113,291, all of which are incorporated herein by reference. Segmented electrodes can also be used for other stimulation techniques including, but not limited to, spinal cord stimulation, peripheral nerve stimulation, dorsal root ganglion stimulation, or stimulation of other nerves, muscles, and tissues.

Figure 3:
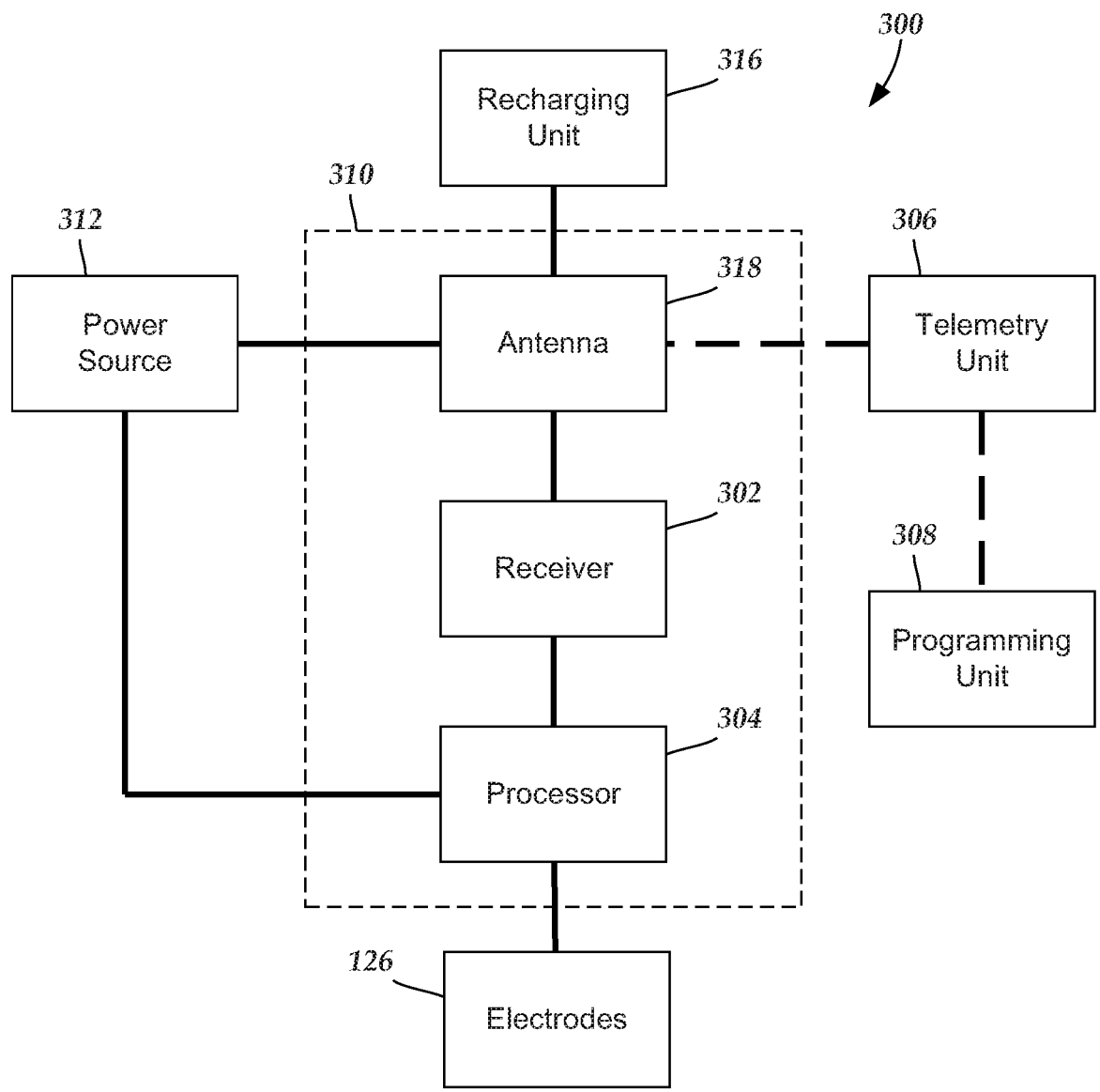
FIG. 3 is a schematic overview of one embodiment of components of a stimulation system, including an electronic subassembly disposed within a control module, according to the invention.

FIG. 3 is a schematic overview of one embodiment of components of an electrical stimulation system 300 including an electronic subassembly 310. It will be understood that the electrical stimulation system can include more, fewer, or different components and can have a variety of different configurations including those configurations disclosed in the stimulator references cited herein.

Some of the components (for example, a power source 312, an antenna 318, a receiver 302, and a processor 304) of the electrical stimulation system can be positioned on one or more circuit boards or similar carriers within a sealed housing of an implantable pulse generator (see e.g., 14 in FIG. 1), if desired. Any power source 312 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bio-energy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 318 or a secondary antenna. The external power source can be in a device that is mounted on the skin of the user or in a unit that is provided near the user on a permanent or periodic basis.

If the power source 312 is a rechargeable battery, the battery may be recharged using the optional antenna 318, if desired. Power can be provided to the battery for recharging by inductively coupling the battery through the antenna to a recharging unit 316 external to the user. Examples of such arrangements can be found in the references identified above.

Figure 4:
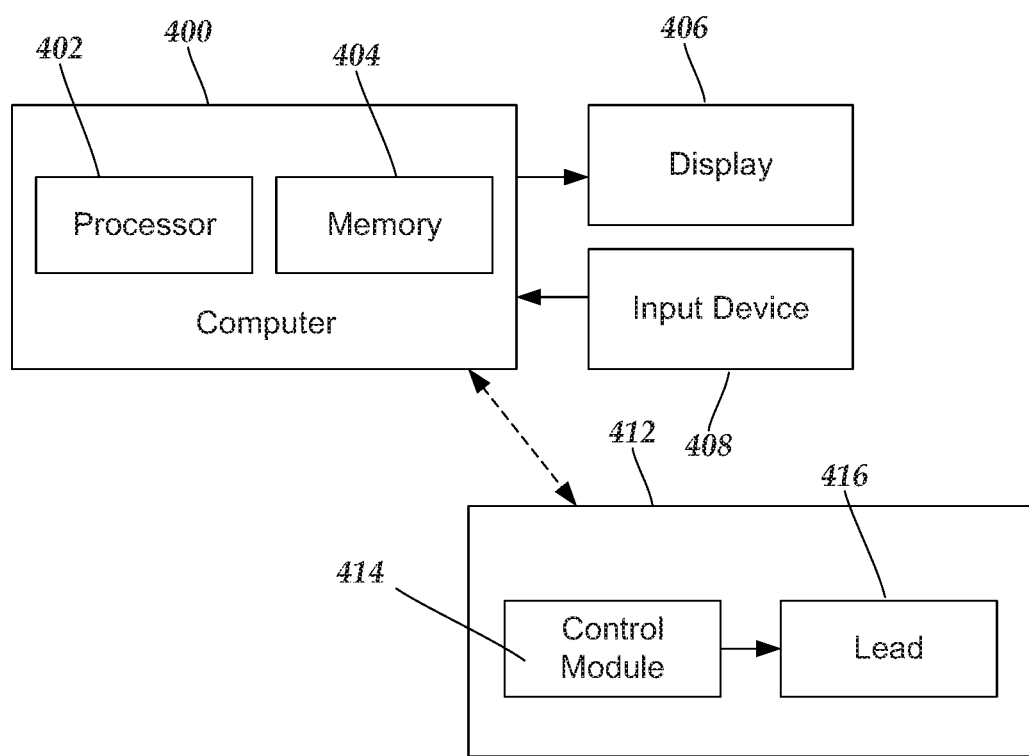
FIG. 4 is a schematic illustration of one embodiment of a system for practicing the invention.

The electronic subassembly 310 and, optionally, the power source 312 can be disposed within a control module (e.g., the IPG 14 or the ETS 20 of FIG. 1). The control module is shown in FIG. 4.

In one embodiment, electrical stimulation signals are emitted by the electrodes 126 on the paddle or lead body to stimulate nerve fibers, muscle fibers, or other body tissues near the electrical stimulation system. The processor 304 is generally included to control the timing and electrical characteristics of the electrical stimulation system. For example, the processor 304 can, if desired, control one or more of the timing, frequency, strength, duration, and waveform of the pulses. In addition, the processor 304 can select which electrodes can be used to provide stimulation, if desired. In some embodiments, the processor 304 selects which electrode(s) are cathodes and which electrode(s) are anodes. In some embodiments, the processor 304 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 308 that, for example, allows modification of pulse characteristics. In the illustrated embodiment, the processor 304 is coupled to a receiver 302 which, in turn, is coupled to the optional antenna 318. This allows the processor 304 to receive instructions from an external source to, for example, direct the pulse characteristics and the selection of electrodes, if desired.

In one embodiment, the antenna 318 is capable of receiving signals (e.g., RF signals) from an external telemetry unit 306 which is programmed by the programming unit 308. The programming unit 308 can be external to, or part of, the telemetry unit 306. The telemetry unit 306 can be a device that is worn on the skin of the user or can be carried by the user and can have a form similar to a pager, cellular phone, or remote control, if desired. As another alternative, the telemetry unit 306 may not be worn or carried by the user but may only be available at a home station or at a clinician's office. The programming unit 308 can be any unit that can provide information to the telemetry unit 306 for transmission to the electrical stimulation system 300. The programming unit 308 can be part of the telemetry unit 306 or can provide signals or information to the telemetry unit 306 via a wireless or wired connection. One example of a suitable programming unit is a computer operated by the user or clinician to send signals to the telemetry unit 306.

The signals sent to the processor 304 via the antenna 318 and the receiver 302 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 300 to cease operation, to start operation, to start charging the battery, or to stop charging the battery. In other embodiments, the stimulation system does not include the antenna 318 or receiver 302 and the processor 304 operates as programmed.

Optionally, the electrical stimulation system 300 may include a transmitter (not shown) coupled to the processor 304 and the antenna 318 for transmitting signals back to the telemetry unit 306 or another unit capable of receiving the signals. For example, the electrical stimulation system 300 may transmit signals indicating whether the electrical stimulation system 300 is operating properly or not or indicating when the battery needs to be charged or the level of charge remaining in the battery. The processor 304 may also be capable of transmitting information about the pulse characteristics so that a user or clinician can determine or verify the characteristics.

FIG. 4 illustrates one embodiment of a system for practicing the invention. The system can include a computer 400 or any other similar device that includes a processor 402 and a memory 404, a display 406, an input device 408, and, optionally, the electrical stimulation system 412.

The computer 400 can be a laptop computer, desktop computer, tablet, mobile device, smartphone or other devices that can run applications or programs, or any other suitable device for processing information and for presenting a user interface. The computer can be, for example, a clinician programmer, patient programmer, or remote programmer for the electrical stimulation system 412. The computer 400 can be local to the user or can include components that are non-local to the user including one or both of the processor 402 or memory 404 (or portions thereof). For example, in some embodiments, the user may operate a terminal that is connected to a non-local computer. In other embodiments, the memory can be non-local to the user.

The computer 400 can utilize any suitable processor 402 including one or more hardware processors that may be local to the user or non-local to the user or other components of the computer. The processor 402 is configured to execute instructions provided to the processor, as described below.

Any suitable memory 404 can be used for the processor 402. The memory 404 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computer.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 406 can be any suitable display device, such as a monitor, screen, display, or the like, and can include a printer. The input device 408 can be, for example, a keyboard, mouse, touch screen, track ball, joystick, voice recognition system, or any combination thereof, or the like and can be used by the user to interact with a user interface or clinical effects map.

The electrical stimulation system 412 can include, for example, a control module 414 (for example, an implantable pulse generator) and a lead 416 (for example, the lead illustrated in FIG. 1.) The electrical stimulation system 412 may communicate with the computer 400 through a wired or wireless connection or, alternatively or additionally, a user can provide information between the electrical stimulation system 412 and the computer 400 using a computer-readable medium or by some other mechanism. In some embodiments, the computer 400 may include part of the electrical stimulation system.

In at least some instances, a medical practitioner may wish to tailor the stimulation parameters (such as which one or more of the stimulating electrode contacts to use, the stimulation pulse amplitude (such as current or voltage amplitude depending on the stimulator being used,) the stimulation pulse width, the stimulation frequency, or the like or any combination thereof) for a particular patient to improve the effectiveness of the therapy. Electrical stimulation systems can provide a user interface that facilitates parameter selections. Examples of such systems and interfaces can be found in, for example, U.S. Pat. Nos. 8,326,433; 8,831,731; 8,849,632; 9,050,470; and 9,072,905; and U.S. Patent Application Publication No. 2014/0277284, all of which are incorporated herein by reference in their entireties.

Figure 5A:
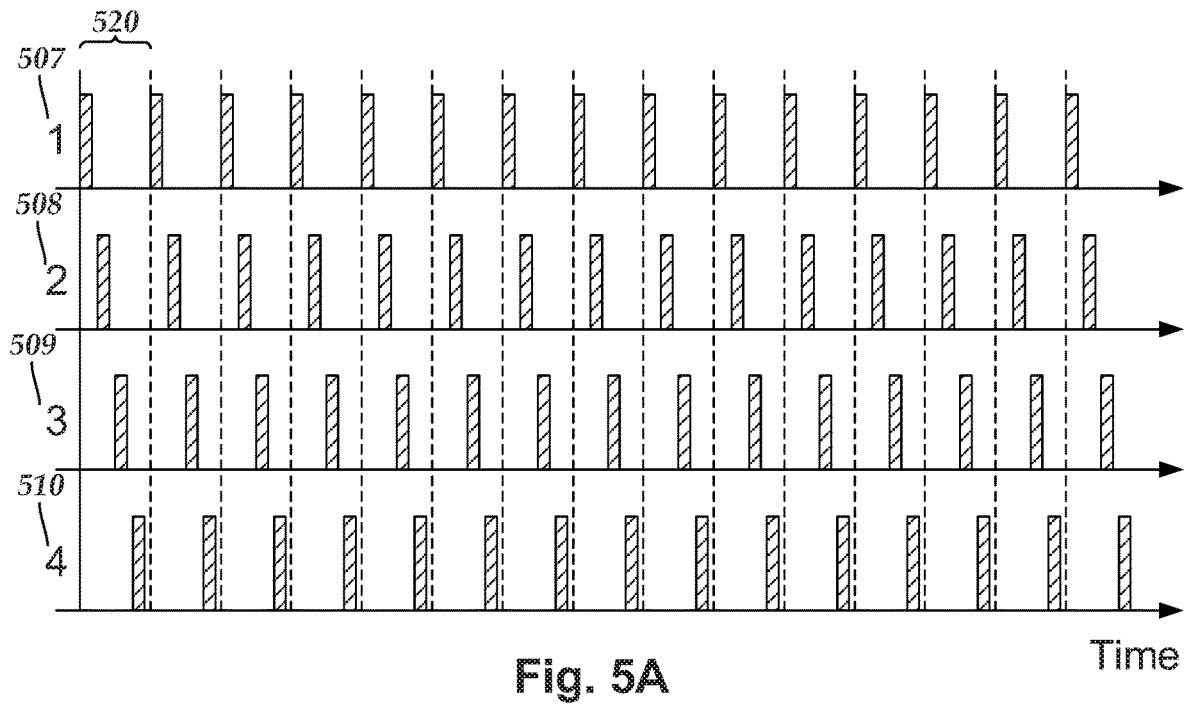
FIG. 5A is a schematic graphical representation of one embodiment of repeating, time-ordered arrangements of stimulation instances, with each of the stimulation instances occurring once, sequentially, and in the same order during each of the repeating arrangements, according to the invention.

Turning to FIG. 5A, conventional stimulation may involve generating a single stimulation field for each lead, such that all electrical pulses emitted from the lead do so at the same time. The stimulation field is typically generated to stimulate as many targeted neurons as feasible, while also avoiding stimulation of as many untargeted neurons as feasible.

At least some neurological conditions (e.g., Parkinsonism, essential tremor, dystonia, or the like) involve populations of neurons in the brain that become overactive. Such over-activity may involve pathological synchronous firings of action potentials along affected parenchymal populations.

Although the invention is not limited to any particular theory, it is thought that electrical stimulation can be used to desynchronize firings of action potentials along at least some neurons of the affected neuron population. For example, asynchronous stimulation can be used to produce a coordinated reset of synchronous action potential firings. In addition to potentially improving efficacy, asynchronous stimulation may also reduce power consumption and reduce undesired side effects caused by continuous stimulation.

One way to provide asynchronous stimulation is to stimulate neurons using multiple stimulation fields. In some instances, the electrodes of one or more leads are used to generate a series of stimulation fields ("fields"), where each field is generated by a different subset of electrodes (although the subsets may be overlapping). Each field has a set of stimulation parameters (e.g., frequency, stimulation duration, pulse width, amplitude, and the like). The stimulation parameters for each field can be either the same or different from the remaining fields. In at least some embodiments, the period for two different stimulation fields are temporally offset from one another. The difference in stimulation timing may reduce, or even prevent, undesired neuronal synchronization. Each field stimulates different subpopulations of neurons with or without temporal or physical overlap with one or more other fields.

The electrodes can either be in close physical proximity to one another, or physically spaced-apart from one another. The electrodes may be disposed along a single implanted lead, or along multiple implanted leads. When multiple leads are utilized, the multiple leads may be coupled to the same control module, or to separate control modules in communication with one another (to coordinate the stimulation timing or stimulation parameters). The electrodes may be implanted at the same target stimulation location or along two different target stimulation locations within the patient. In at least some embodiments, the two or more electrodes are implanted within the patient's brain.

It is thought, although not necessary to the invention, that the electrical stimulation signals generated by the two or more electrodes generate effective electric fields (e.g., electrical stimulation propagating from the electrodes sufficient to cause an excitatory effect on axons surrounding the electrodes) that function to reset the undesired neural activity in a coordinated manner.

The electrodes may employ the same stimulation parameters, or may have one or more different stimulation parameters. The size and shape of the effective electric fields generated by the electrodes is based on the set of stimulation parameters used to generate the stimulation. In at least some instances, the size and shape of the effective electric fields generated by the two or more electrodes (or sets of electrodes) at a given set of stimulation parameters can be estimated, using one or more computer models (e.g., Volume of Tissue Activated Model, Stimulation Field Model, or the like or combinations thereof). In at least some embodiments, the effective volume of an electric field can be based on the region of tissue that experiences a stimulating effect in response to the electric field. Outside this effective volume, the electric field may be too weak to stimulate the tissue. Although sub-threshold stimulation may also provide some effects, the computer models may facilitate selection of implantation locations, or facilitate selection of stimulation parameters, or both. Examples of methods for determining the volume of activation can be found in, for example, U.S. Pat. Nos. 7,346,282; 8,180,601; 8,209,027; 8,326,433; 8,589,316; 8,594,800; 8,606,360; 8,675,945; 8,831,731; 8,849,632; 8,958,615; 9,020,789; and U.S. Patent Application Publications Nos. 2009/0287272; 2009/0287273; 2012/0314924; 2013/0116744; 2014/0122379; 2015/0066111; and 2016/0030749, all of which are incorporated herein by reference.

In some embodiments, the electrodes generate effective electric fields that are temporally offset (e.g., time-delayed) from one another so that the effective electric fields are out of phase from one another. In at least some embodiments, the electrodes are situated such the effective electric fields generated by the electrodes stimulate different populations of neurons in communication with one another (e.g., different neurons along a particular neural pathway). Although not wishing to be bound by a particular theory, the offsetting of the effective electric fields generated by the electrodes may be such that the downstream neurons are in a refractory period while the upstream neurons are propagating action potentials. In which case, the action potentials may be unable to propagate from the upstream neurons to the downstream neurons. Accordingly, undesired synchronized neuronal activity may be disrupted.

Any suitable time delay may be implemented between the electrodes. In some embodiments, the time delay may be determined by testing and observation. In some embodiments, the time delay is determined based on the frequency of the undesired neural activity (e.g., an observed shifted theta-band frequency) to be desynchronized or disrupted.

When the generated effective electric fields are time-delayed from one another, in some embodiments it may be desirable for the different electric fields to have little or no physical overlap. This may facilitate coordination the resetting of the action potential propagation by stimulating different populations of cells that are in communication with one another. When there is substantial physical overlap of effective electric fields between the electrodes, the stimulation parameters of the electrodes may be varied from one another in order to preferentially target some neurons more than others.

It has been shown that some stimulation parameters may preferentially target some neurons more than others. At least some physical characteristics of neurons (e.g., axon diameters, the presence or absence of a myelin sheath, or the like) may affect whether or not those neurons are excited by an effective electric field having a particular set of stimulation parameters. Consequently, in at least some embodiments, the stimulation parameters of at least one of the generated effective electric fields is varied in response to one or more physical characteristics of the neurons along the overlapping portion of the generated effective electric fields (e.g., axon diameters, the presence or absence of a myelin sheath, or the like).

The different stimulation parameters may enable a first set of stimulation parameters of a first electrode (or set of electrodes) to stimulate a first set of target neurons and a second set of stimulation parameters of a second electrode (or set of electrodes) to stimulate a second set of target neurons. In some embodiments, the second set of target neurons is a subset of the first set of target neurons. In which case, one narrow example of a stimulation procedure may include only a portion of the overall population of neurons within an overlapping portion of the effective electric fields becoming excitable during stimulation by a first electrode (or set of electrodes) with a first set of stimulation parameters, while all (or nearly all) of the overall population of neurons within the overlapping portion of the effective electric fields becoming excitable during stimulation by a second electrode with a second set of stimulation parameters.

In other embodiments, the second set of target neurons is mutually exclusive of the first set of target neurons. In which case, one example of a stimulation procedure may include a first portion of the overall population of neurons within an overlapping portion of the effective electric fields becoming excitable during stimulation by a first electrode (or set of electrodes) with a first set of stimulation parameters, and a second portion (mutually exclusive of the first portion) of the overall population of neurons within the overlapping portion of the effective electric fields becoming excitable during stimulation by a second electrode (or set of electrodes) with a second set of stimulation parameters.

In at least some embodiments, stimulation can be timed between the two or more electrodes such that some neurons are in a refractory period while other neurons are propagating action potentials. In which case, at least some of the action potentials are unable to propagate along the entire length of the neural pathway. Accordingly, undesired neural activity may be disrupted through desynchronization.

In at least some instances it may be a disadvantage to continuously stimulate a patient to provide therapy. Accordingly, it may sometimes be useful to stimulate patient tissue intermittently. Intermittent stimulation can be implemented in different ways, such as in a "flashing" manner.

Continuous stimulation can consume large amounts of power compared to intermittent (e.g., flashing) stimulation, thereby reducing the lifespan of power source of an IPG. Additionally, decreased efficacy and increased undesired side effects may also result more quickly from continuous stimulation, as compared to intermittent (e.g., flashing) stimulation.

As described herein, intermittent stimulation can be generated corresponding to a combination of a repeating, time-ordered arrangement of stimulation instances and an ON/OFF-switch pattern. Each arrangement of stimulation instances includes multiple stimulation instances occurring exactly once. The ON/OFF-switch pattern alternates between ON and OFF periods over time and operates independently from the repeating arrangement of stimulation instances.

An intermittent stimulation program is generated that corresponds to repetition of the arrangement of stimulation instances with omission of stimulation instances occurring during the OFF periods of the ON/OFF-switch pattern. In at least some embodiments, the intermittent stimulation program is used to generate intermittent stimulation of patient tissue. The intermittent stimulation can, for example, be implemented using electrodes disposed along an implantable electrical stimulation lead. In least some embodiments, the generated stimulations correspond to different individual electrodes or subsets of electrodes of the electrical stimulation lead.

In at least some embodiments, the intermittent stimulation program is used in conjunction with other techniques for discontinuing stimulation over time. For example, a stimulation system may be programmed to stimulate patient tissue over a period of time of a few minutes per day (or per week, or per month, or the like). In such instances, the intermittent stimulation program described herein can be used during some or all of these periods of stimulation. Such a stimulation paradigm is one of many possible stimulation paradigms and is not meant to be limiting.

FIG. 5A shows a graphical representation of one embodiment of repeating, time-ordered arrangements of stimulation instances. In FIG. 5A (and in subsequent figures) each arrangement, such as arrangement 520, includes four stimulation instances: stimulation instance 1 507, stimulation instance 2 508, stimulation instance 3 509, and stimulation instance 4 510. Each stimulation instance 507-510 occurs once during each arrangement 520. In at least some embodiments, the time-ordered arrangements of stimulation instances occur in a predetermined order in time.

It will be understood that arrangements providing four stimulation instances is exemplary and not meant to be limiting. Arrangements can include any suitable number of stimulation instances (e.g., 2, 3, 4, 5, 6, 7, 8, 9, 10, 11, 12, 13, 14, 15, 16, or more stimulation instances).

Each of the stimulation instances includes a set of stimulation parameters, such as stimulation duration, frequency, pulse width, amplitude, and the like. In some embodiments, each of the stimulation instances of the arrangements is provided using the same stimulation parameters. In alternate embodiments, for each arrangement, one or more of the stimulation instances is provided using different stimulation parameters than at least one other stimulation instances. In at least some embodiments, for each arrangement, each of the stimulation instances has different stimulation parameters than the remaining stimulation instances.

In at least some embodiments, the recurring stimulation instances 507-510 occur sequentially and in the same order within each arrangement 520 with each of the stimulation instances occurring exactly once. In FIG. 5A, the stimulation instances occur in the sequence: 1, 2, 3, 4. Any variation of this scheme can be used including, for example, 1, 2, 3, 4; 1, 2, 4, 3; 1, 3, 2, 4; 1, 3, 4, 2; 1, 4, 2, 3; 1, 4, 3, 2; 2, 1, 3, 4; 2, 1, 4, 3; 2, 3, 1, 4; 2, 3, 4, 1; 2, 4, 1, 3; 2, 4, 3, 1; 3, 1, 2, 4; 3, 1, 4, 2; 3, 2, 1, 4; 3, 2, 4, 1; 3, 4, 1, 2; 3, 4, 2, 1; 4, 1, 2, 3; 4, 1, 3, 2; 4, 2, 1, 3; 4, 2, 3, 1; 4, 3, 1, 2; and 4, 3, 2, 1. Note that, in embodiments where the stimulation instances occur sequentially and in the same order within each repeating arrangement with each of the stimulation instances occurring exactly once, the potential number of different possible combinations varies with the number of different stimulation instances.

As mentioned above, an intermittent stimulation program is generated that corresponds to repetition of the arrangement of stimulation instances with omission of stimulation instances occurring during the OFF periods of an ON/OFF-switch pattern combined with the repeating arrangement of stimulation instances. The intermittent stimulation program can then be used to generate a flashing stimulation pattern for stimulating patient tissue using, for example, electrodes disposed along an implantable electrical stimulation lead.

In least some embodiments, recurring stimulations corresponding to the different stimulation instances of the arrangements, in turn, correspond to different individual electrodes or subsets of electrodes of the electrical stimulation lead. The stimulations can each be discretely emitted from different electrodes of one or more leads (e.g., electrodes 26 of leads 12 in FIG. 1). Alternately, or additionally, one or more of the stimulations can be collectively emitted from multiple electrodes of a lead in varying distributions of stimulation energy. For example, a given stimulation may include 20% of the stimulation energy delivered from a first electrode, while 80% of the stimulation energy delivered from a second electrode. Other distributions of stimulation energy and other combinations of electrodes can be incorporated into a "stimulation", thereby providing many different possible stimulation patterns suitable for generating stimulation fields of many different complex sizes and shapes. It will be understood that arrangements can include any suitable number of recurring stimulations from any suitable number of electrodes (e.g., 2, 3, 4, 5, 6, 7, 8, 9, 10, 11, 12, 13, 14, 15, 16, or more electrodes).

Figure 5B:
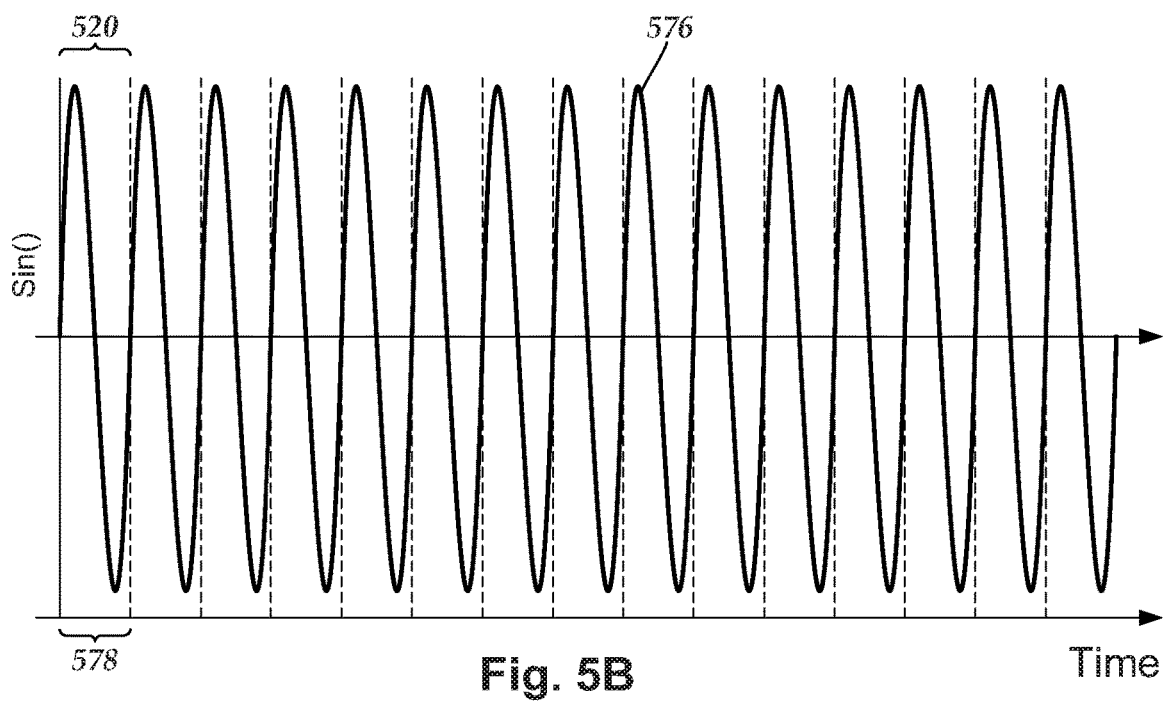
FIG. 5B is a schematic graphical representation of one embodiment of a sine wave representing a pathological oscillation of a neuronal population, according to the invention.

Turning to FIG. 5B, an arrangement, such as arrangement 520, may be any suitable length of time, but is typically in the millisecond or second range of time. In at least some embodiments, the time interval of the repeating arrangement corresponds to a period of oscillation of a neuronal population in proximity to electrodes of one or more electrical stimulation leads when the one or more electrical stimulation leads are implanted into a patient with the electrodes of the lead(s) positioned at a target stimulation location.

It may be advantageous to generate arrangements that occur over time periods that correspond to frequency ranges (e.g., pathological oscillations) associated with a neuronal population to ensure that generated stimulations corresponding to the stimulation instances of the arrangements are emitted at the same relative phases as the frequency ranges associated with the neuronal population over time. Computer modelling has shown efficacy for reducing symptoms of Parkinson's disease when generated stimulations occur at the same relative phases of pathological oscillations.

FIG. 5B shows a sine wave 576 graphed over time. The sine wave 576 represents a pathological frequency associated with a neuronal population occurring in proximity to electrodes of an implanted electrical stimulation lead. Vertical dashed lines depict boundaries between adjacent periods of the sine wave 576, such as period 578. As shown in FIG. 5B, the periods 578 of the sine wave 576 are equal in length to the repeating arrangements 520. Determining the period of the pathological frequency, in order to match a period of an arrangement with such a period, can be performed using any suitable technique including, for example, experimental determination, statistical/computer modeling, clinical determination, or the like or combinations thereof.

Figure 5C:
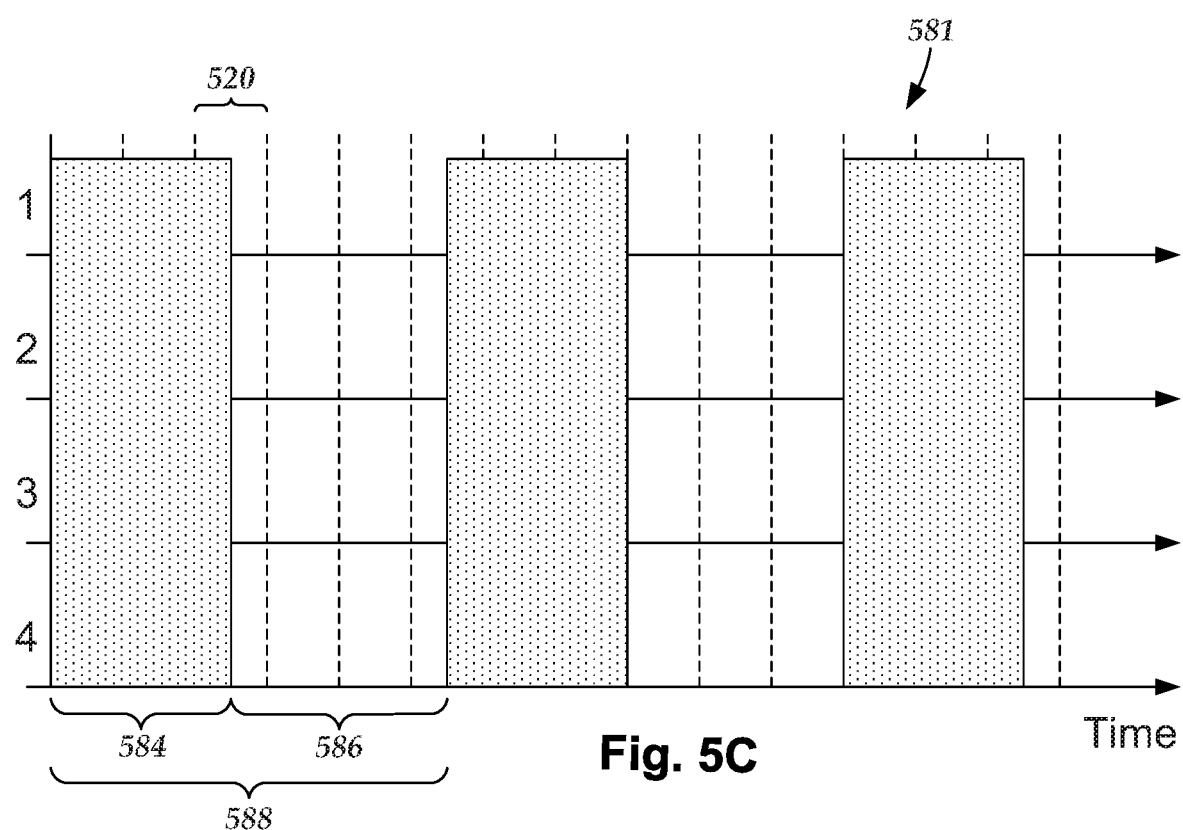
FIG. 5C is a schematic graphical representation of one embodiment of an ON/OFF switch pattern that includes alternating ON periods and OFF periods, according to the invention.

Turning to FIG. 5C, stopping and restarting stimulation to obtain intermittent stimulation may be difficult, time-consuming, and/or energy-consuming. Attempting to maintain continuity of phase with a targeted neuronal oscillation while stopping and restarting stimulation may be especially difficult. Typically, restarting a previous stimulation begins the stimulation at the beginning of a stimulation period, regardless of where along a stimulation period stimulation previously ceased, thereby adding an additional layer of complexity to maintaining continuity of phase of a targeted neuronal oscillation with the intermittent stimulation.

As described below, an intermittent stimulation program is generated that corresponds to a ON/OFF-switch pattern combined with a time-ordered arrangement of stimulation instances. The intermittent stimulation program is suitable for combining with a pulse generator and electrodes for providing intermittent (e.g., flashing) stimulation, while also maintaining phase alignment with a targeted neuronal oscillation when synched with that oscillation.

The one or more ON/OFF-switch patterns alternate between ON periods and OFF periods. The ON/OFF-switch patterns function to mute recurring stimulation instances of the repeating arrangements of stimulation instances when those stimulation instances occur while the ON/OFF-switch pattern is in an OFF period. The muting of stimulation instances can be used to generate an intermittent stimulation program that, in turn, can be used to generate stimulations in an intermittent (e.g., flashing) manner.

The repeating arrangement of stimulation instances operates independently from the ON/OFF-switch pattern(s) and continues to sequentially alternate between different stimulation instances over time, regardless of whether the ON/OFF-switch pattern is in an ON or OFF period. Consequently, continuity of phase of the targeted neuronal oscillation can be maintained with the recurring stimulation instances (and corresponding stimulations) between successive ON periods without needing to expend effort into repeatedly retuning the stimulations in order to maintain a phase alignment.

FIG. 5C shows a graphical representation of one embodiment of an ON/OFF-switch pattern 581 implemented over time. The ON/OFF-switch pattern 581 is shown alternating between an ON period 584 and an OFF period 586 according to a schedule of repeating ON/OFF-switch periods, such as ON/OFF-switch period 588. Vertical dashed lines depict time intervals between adjacent arrangements of stimulation instances, such as arrangement 520. In FIG. 5C, and in other figures, the ON period 584 is shown as a stippled block, while the OFF period 586 is shown as a transparent region between one or more adjacent ON periods 584.

The ON/OFF-switch periods can be any suitable length (i.e., time interval). In FIG. 5C, the ON/OFF-switch periods 588 are shown extending over 5.5 arrangements 520. Additionally, the ON periods and the OFF periods within the ON/OFF-switch periods can have any suitable lengths (i.e., time intervals). In at least some embodiments, at least one of the ON periods or one of the OFF periods is longer than a combined stimulation duration of two consecutive stimulation instances. In some embodiments, the time interval of the ON period 584 is equal to the time interval of the OFF period 586. In some embodiments, the time interval of the ON period 584 is larger than the time interval of the OFF period 586. In some embodiments, the time interval of the ON period 584 is smaller than the time interval of the OFF period 586. In FIG. 5C, for each ON/OFF-switch period 588, the ON period 584 extends over 2.5 arrangements 520 and the OFF period 586 extends over 3 arrangements 520.

Figure 6A:
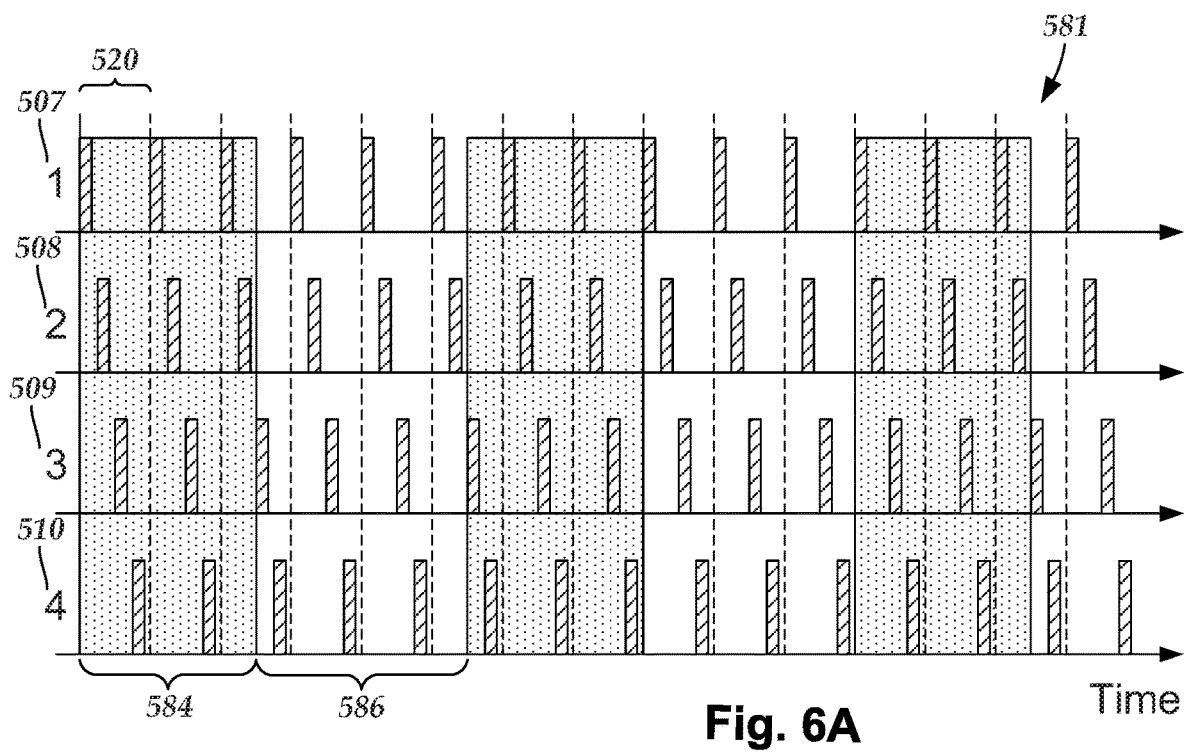
FIG. 6A is a schematic graphical representation of one embodiment of the repeating, time-ordered arrangements of stimulation instances of FIG. 5A overlaid onto the ON/OFF-switch pattern of FIG. 5C, according to the invention.

FIG. 6A shows one embodiment of a graphical representation of the repeating arrangements of stimulation instances 520 overlaid onto the ON/OFF-switch pattern 581. As shown in FIG. 6A, for each repeating stimulation instance 507-510, some of the stimulation instances occur while the ON/OFF-switch pattern 581 is in an ON period, such as ON period 584, and some of the stimulations occur while the ON/OFF-switch pattern 581 is in an OFF period, such as the OFF period 586.

Figure 6B:
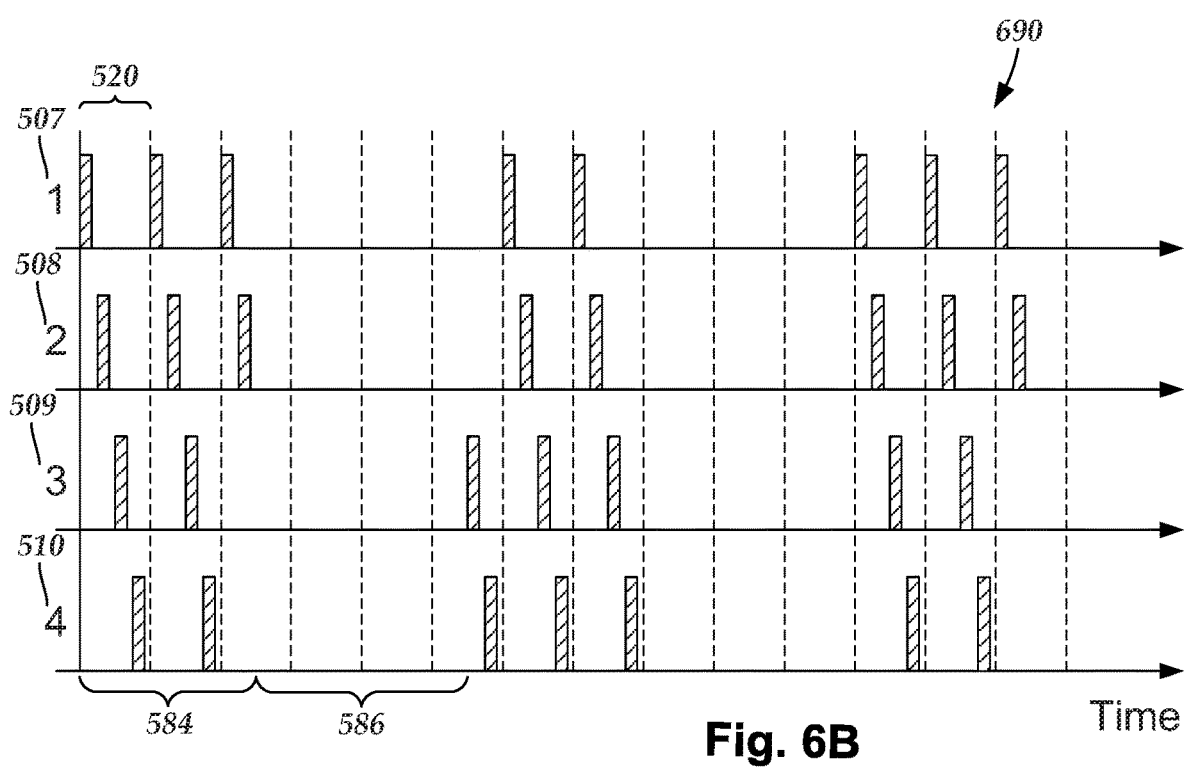
FIG. 6B is a schematic graphical representation of one embodiment of an intermittent stimulation program corresponding to a combination of the repeating, time-ordered arrangements of stimulation instances of FIG. 6A and the ON/OFF-switch pattern of FIG. 6A, according to the invention.

FIG. 6B shows a graphical representation of one embodiment of an intermittent stimulation program 690 corresponding to a combination of the repeating arrangements of stimulation instances 520 and the ON/OFF-switch pattern 581. As shown in FIG. 6B, the intermittent stimulation program 690 includes those recurring stimulation instances occurring while the ON/OFF-switch pattern 581 is in one of the recurring ON periods 584 and omits those recurring stimulation instances occurring while the ON/OFF-switch pattern 581 is in one of the recurring OFF periods 586. As also shown in FIG. 6B, since the ON/OFF-switch pattern alternates between ON and OFF periods independently from the repeating arrangements of stimulation instances the timing of the recurring stimulation instances of the repeating arrangements is maintained by the intermittent stimulation program, regardless of where along a given arrangement of stimulation instances the ON/OFF-switch pattern alternates between the ON and OFF periods (and/or between OFF and ON periods).

Figure 7A:
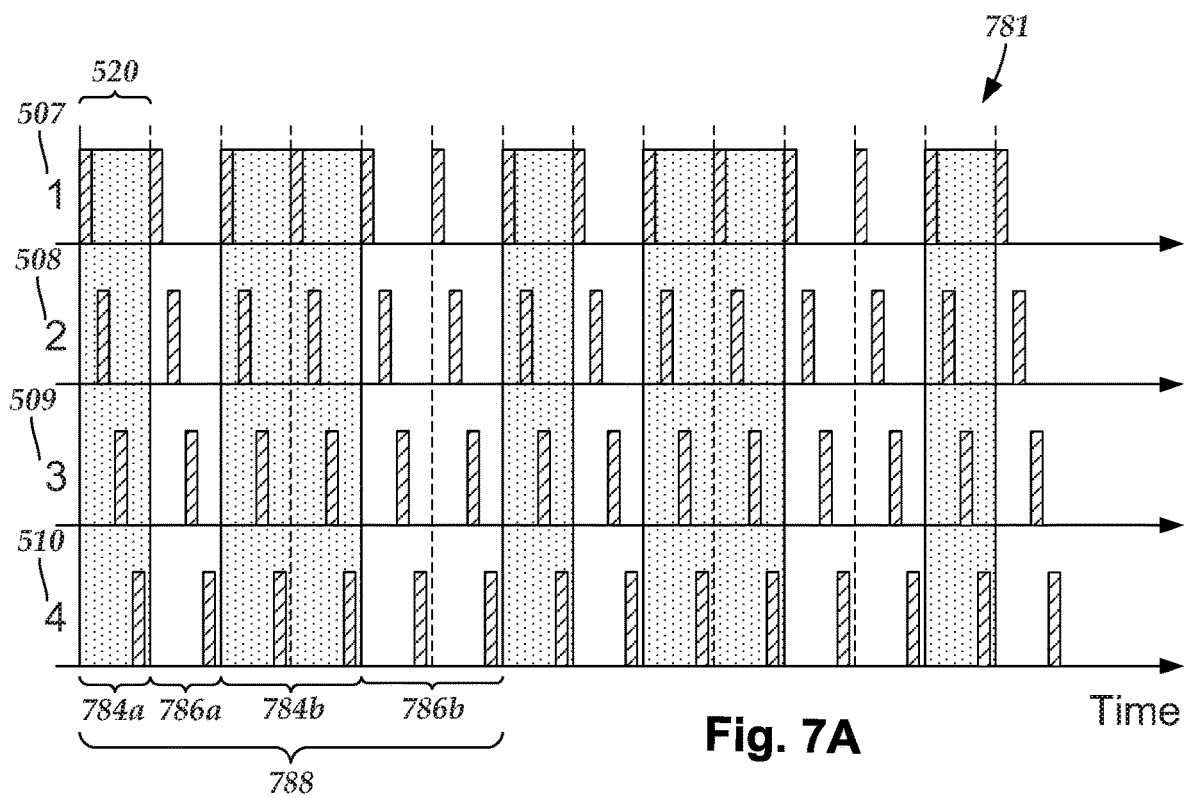
FIG. 7A is a schematic graphical representation of a second embodiment of an ON/OFF-switch pattern and the repeating arrangements of stimulation instances of FIG. 5A, the ON/OFF-switch pattern alternating between ON and OFF periods according to a repeating ON/OFF-switch period that includes multiple ON and OFF periods, according to the invention.

Turning to FIG. 7A, in FIGS. 5C and 6A the repeating ON/OFF-switch periods of the ON/OFF-switch pattern are shown to each include a single ON period and a single OFF period. In at least some embodiments, the ON/OFF-switch periods each include multiple ON periods and multiple OFF periods, where at least one of the ON periods or at least one of the OFF periods has a different length (i.e., time interval) than at least one other ON or OFF period of the ON/OFF-switch period.

FIG. 7A shows a graphical representation of another embodiment of the repeating arrangements of stimulation instances 520 overlaid onto an ON/OFF-switch pattern 781. The ON/OFF-switch pattern 781 includes repeating ON/OFF-switch periods, such as ON/OFF-switch period 788. Each ON/OFF-switch period 788 includes a first ON period 784a, a first OFF period 786a, a second ON period 784b, and a second OFF period 786b. As shown in FIG. 7A, some of the stimulation instances align with the ON/OFF-switch pattern 781 when in one of the recurring ON periods 784a-b while some other of the stimulation instances align with the ON/OFF-switch pattern 781 when in one of the recurring OFF periods 786a-b.

The ON/OFF-switch periods can be any suitable duration. The ON/OFF-switch periods 788 shown in FIG. 7A each extend along 6 arrangements of stimulation instances 520. ON/OFF-switch patterns with multiple ON/OFF periods can have any suitable number of ON and OFF periods (e.g., 2, 3, 4, 5, 6, 7, 8, or more of each). The individual ON and OFF periods within a given ON/OFF-switch period can have any suitable duration relative to one another.

In at least some embodiments, the ON periods of the ON/OFF-switch pattern are of equal duration to the OFF periods. In at least some embodiments, the ON periods of the ON/OFF-switch pattern are of unequal duration to OFF periods. In at least some embodiments, the ON periods of the ON/OFF-switch pattern are of uniform (i.e., equal) duration. In at least some embodiments, the ON periods of the ON/OFF-switch pattern are of non-uniform (i.e., unequal) duration. In at least some embodiments, the OFF periods of the ON/OFF-switch pattern are of uniform duration. In at least some embodiments, the OFF periods of the ON/OFF-switch pattern are of non-uniform duration.

In some embodiments, the collective durations of the ON periods 784a-b of the ON/OFF-switch periods are equal to the collective durations of the OFF periods 786a-b. In some embodiments, the collective durations of the ON periods 784a-b of the ON/OFF-switch periods are larger than the collective durations of the OFF periods 786a-b. In some embodiments, the collective durations of the ON periods 784a-b of the ON/OFF-switch periods are smaller than the collective durations of the OFF periods 786a-b. In FIG. 7A, for each ON/OFF-switch period 788, the first ON period 784a is shown extending along 1 arrangement of stimulation instances 520, the second ON period 884b along 2 arrangements of stimulation instances 520, the first OFF period 886a along 1 arrangement of stimulation instances 520, and the second OFF period 886b along 2 arrangements of stimulation instances 520.

Figure 7B:
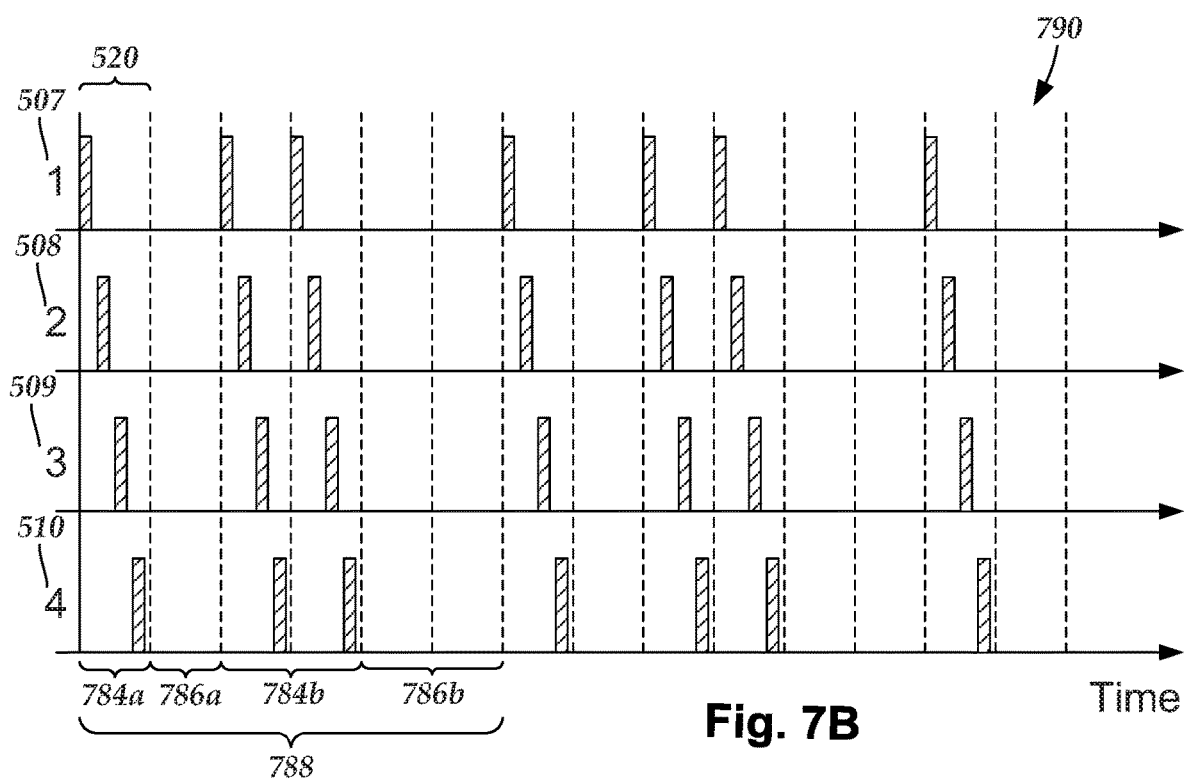
FIG. 7B is a schematic graphical representation of one embodiment of an intermittent stimulation program corresponding to a combination of the repeating, time-ordered arrangements of stimulation instances of FIG. 7A and the ON/OFF-switch pattern of FIG. 7A, according to the invention.

FIG. 7B shows a graphical representation of one embodiment of an intermittent stimulation program 790 corresponding to a combination of the repeating arrangements of stimulation instances 520 and the ON/OFF-switch pattern 781. As shown in FIG. 7B, the intermittent stimulation program 790 includes those stimulation instances occurring while the ON/OFF-switch pattern 781 is in one of the recurring ON periods 784 and omits those stimulation instances occurring while the ON/OFF-switch pattern 781 is in one of the recurring OFF periods 786. As also show in FIG. 7B, since the ON/OFF-switch pattern alternates between ON and OFF periods independently from the repeating arrangements of stimulation instances the timing of the recurring stimulation instances of the repeating arrangements is maintained by the intermittent stimulation program, regardless of where along a given arrangement of stimulation instances the ON/OFF-switch pattern alternates between the ON and OFF periods (and/or between OFF and ON periods).

Figure 8A:
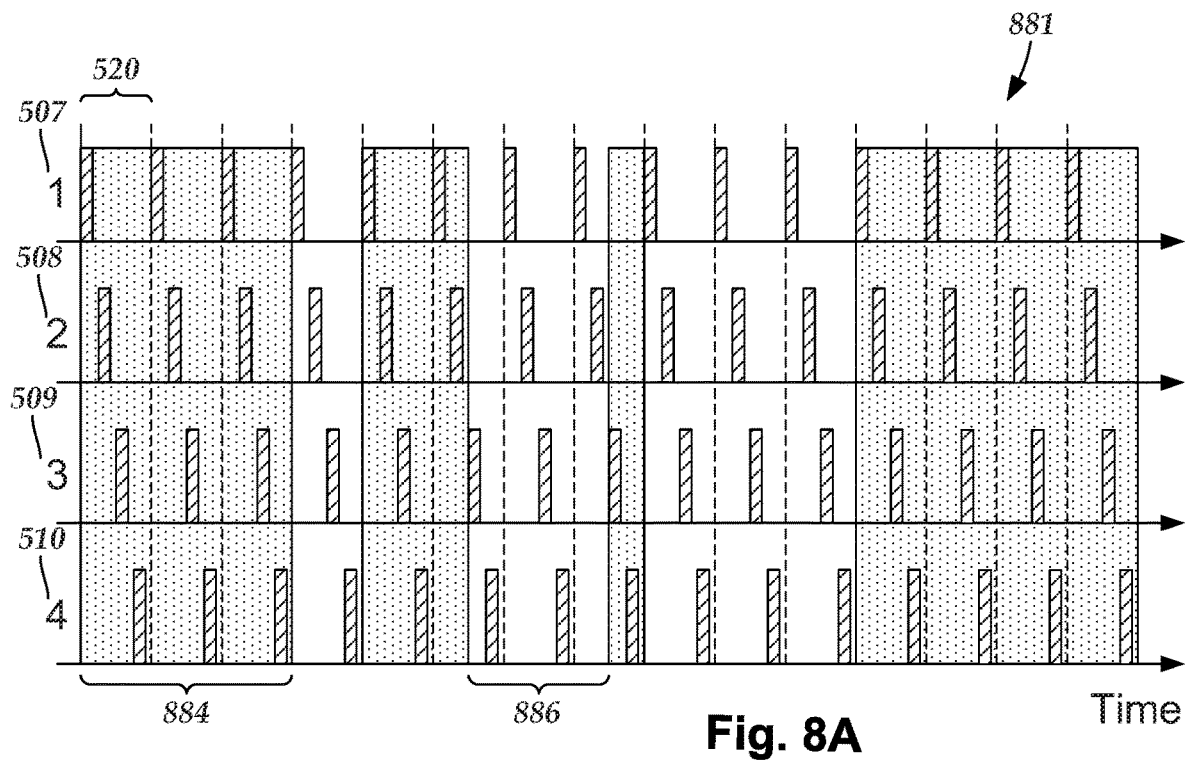
FIG. 8A is a schematic graphical representation of a third embodiment of an ON/OFF-switch pattern and the repeating arrangements of stimulation instances of FIG. 5A, the ON/OFF-switch pattern randomly alternating between ON and OFF periods, according to the invention.

Turning to FIG. 8A, in FIGS. 5C, 6A, and 7A the ON/OFF-switch pattern is shown as repeating ON/OFF-switch periods, with each ON/OFF-switch period alternating between one or more ON and OFF periods according to a set schedule. Alternately, in at least some embodiments the ON/OFF-switch pattern does not include set ON/OFF-switch periods and, instead, alternates between ON and OFF periods in a randomly-determined manner.

The transitions between ON and OFF periods can be randomly determined using any suitable technique. The random determinations of whether to stay in one of an ON or OFF period or to alternate to the other can be determined along any suitable time intervals including, for example, every 10 milliseconds, 50 milliseconds, 100 milliseconds, 500 milliseconds, 1 second, 2 seconds, 3 seconds, 5 seconds, 10 seconds, 15 seconds, 20 seconds, 25 seconds 30 seconds, 40 seconds, or longer. In at least some embodiments, random determinations of whether to stay in one of an ON or OFF period or to alternate to the other period is determined at least once during every arrangement of stimulation instances. The transitions could also be deterministically determined (e.g., following a chaotic pattern). There could also be combinations between deterministic and random generation.

In at least some embodiments, the transitions are variable and determined based on a distribution function that can be disposed about a center stimulation frequency or period. In at least some embodiments, the distribution function that is used to determine the temporal separation between transitions is a periodic repeating distribution function. In some embodiments, the periodic repeating distribution function is a sine wave. It will be understood that other distribution functions can be used include, but are not limited to, a normal distribution, a square wave function, a triangular function, a gamma distribution function, and the like.

The repeating function may be repeated in either a periodic or aperiodic manner with variation in the separation between the repeating functions. In at least some of these instances, there can be one or more distribution variables that may be selectable by a clinician, a patient, or both to define a shape of the distribution. In at least some embodiments, the probability of the next transition can depend on the previous transition(s). In some embodiments, the distribution function is reset by a triggering occurrence, such as the end of the preceding pulse (or even the beginning of the preceding pulse with the distribution function being zero during the preceding pulse).

FIG. 8A shows a graphical representation of another embodiment of the repeating arrangements of stimulation instances 520 overlaid onto an ON/OFF-switch pattern 981. The ON/OFF-switch pattern 881 is shown alternating between ON periods, such as ON period 784, and OFF periods, such as OFF period 786, in a randomly-determined manner.

In FIG. 8A, each ON period and each OFF period of the ON/OFF-switch patterns are of different lengths, for clarity of illustration. The random determinations of whether to stay in one of an ON or OFF period or to alternate to the other can be determined along any suitable time interval including, for example, every 10 milliseconds, 50 milliseconds, 100 milliseconds, 500 milliseconds, 1 second, 2 seconds, 3 seconds, 5 seconds, or longer. In at least some embodiments, random determinations of whether to stay in one of an ON or OFF period or to alternate to the other is determined at least once during every arrangement of stimulation instances 520.

Figure 8B:
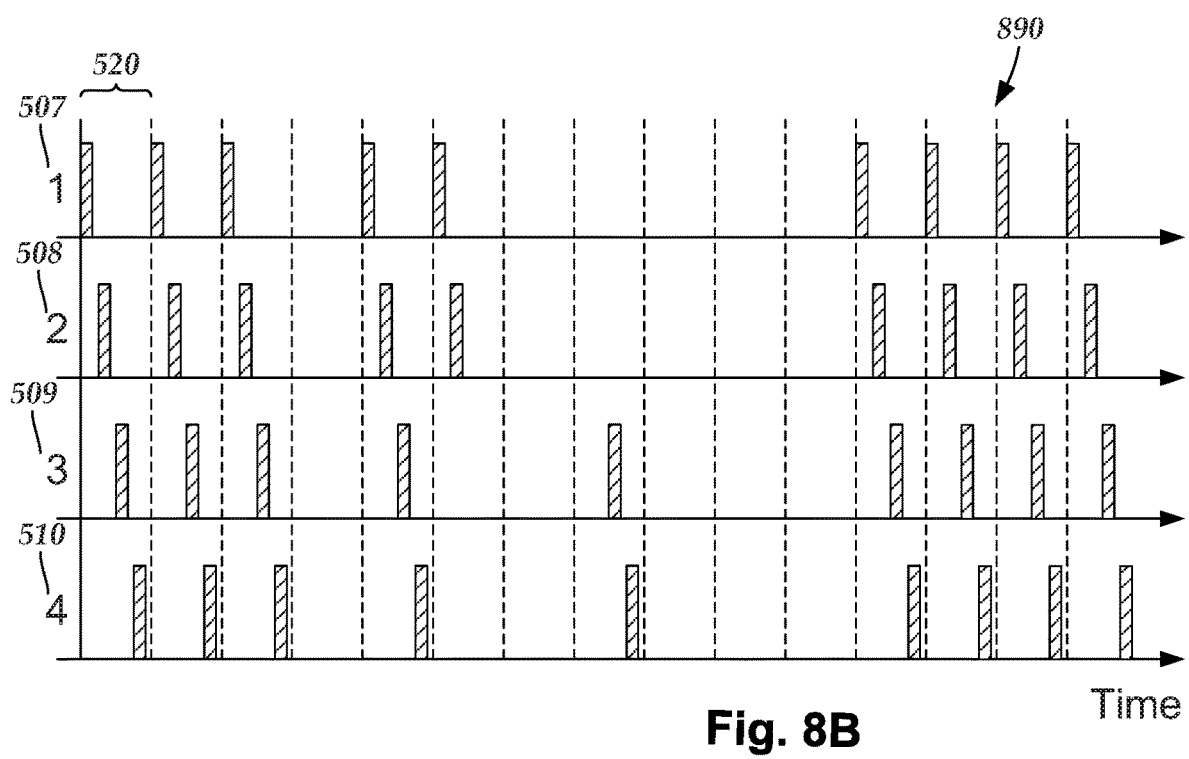
FIG. 8B is a schematic graphical representation of one embodiment of an intermittent stimulation program corresponding to a combination of the repeating arrangements of stimulation instances of FIG. 8A and the randomly alternating ON/OFF-switch pattern of FIG. 8A, according to the invention.

FIG. 8B shows a graphical representation of one embodiment of an intermittent stimulation program 890 corresponding to a combination of the randomly alternating ON/OFF-switch pattern 881 and the repeating arrangements of stimulation instances 520. As shown in FIG. 8B, the intermittent stimulation program 890 includes those stimulation instances occurring while the ON/OFF-switch pattern 881 is in an ON period 884 and omits those stimulation instances occurring while the ON/OFF-switch pattern 881 is in an OFF period 886. As also shown in FIG. 8B, since the ON/OFF-switch pattern alternates between ON and OFF periods independently from the repeating arrangements of stimulation instances the timing of the recurring stimulation instances of the repeating arrangements is maintained by the intermittent stimulation program, regardless of where along a given arrangement of stimulation instances the ON/OFF-switch pattern alternates between the ON and OFF periods (and/or between OFF and ON periods).

Figure 9A:
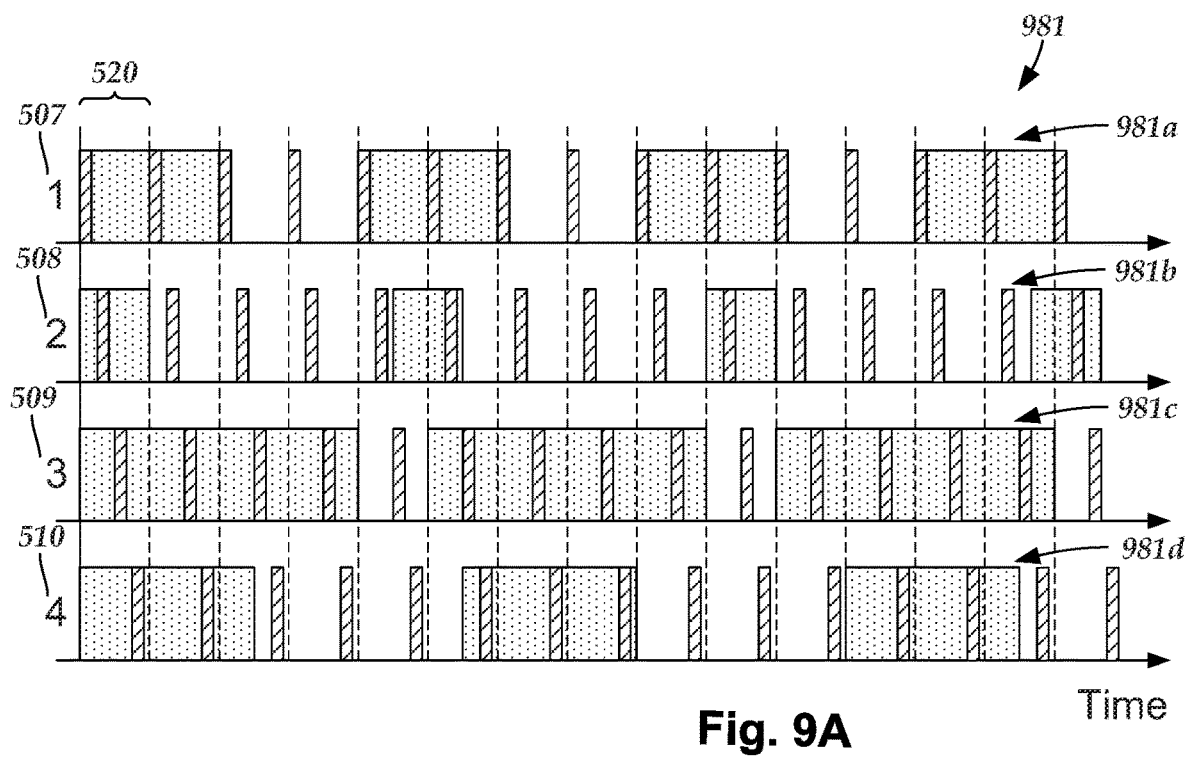
FIG. 9A is a schematic graphical representation of one embodiment of an ON/OFF-switch pattern with multiple sub-patterns and the repeating arrangements of stimulation instances of FIG. 5A, each of the different ON/OFF-switch sub-patterns combined with a different recurring stimulation instance of the repeating arrangements of stimulation instances, according to the invention.

Turning to FIG. 9A, in at least some embodiments, the ON/OFF-switch pattern includes one or more sub-patterns that are applicable only to a subset of the stimulation instances. In which case, the intermittent stimulation program may include repetition of the arrangement of stimulation instances with omission of each of a subset of stimulation instances occurring during the OFF periods of the ON/OFF-switch sub-pattern. For example, the stimulation instances may include a first stimulation instance and a second stimulation instance, where the ON/OFF-switch pattern includes a first ON/OFF-switch sub-pattern applicable only to the first stimulation instance, and where the intermittent stimulation program includes repetition of the arrangement of stimulation instances with omission of each of the first stimulation instances occurring during the OFF periods of the first ON/OFF-switch sub-pattern. Additionally, the ON/OFF-switch pattern may include a second ON/OFF-switch sub-pattern that is applicable only to the second stimulation instance, where the intermittent stimulation program includes repetition of the arrangement of stimulation instances with omission of each of the second stimulation instances occurring during the OFF periods of the second ON/OFF-switch sub-pattern.

Figure 9B:
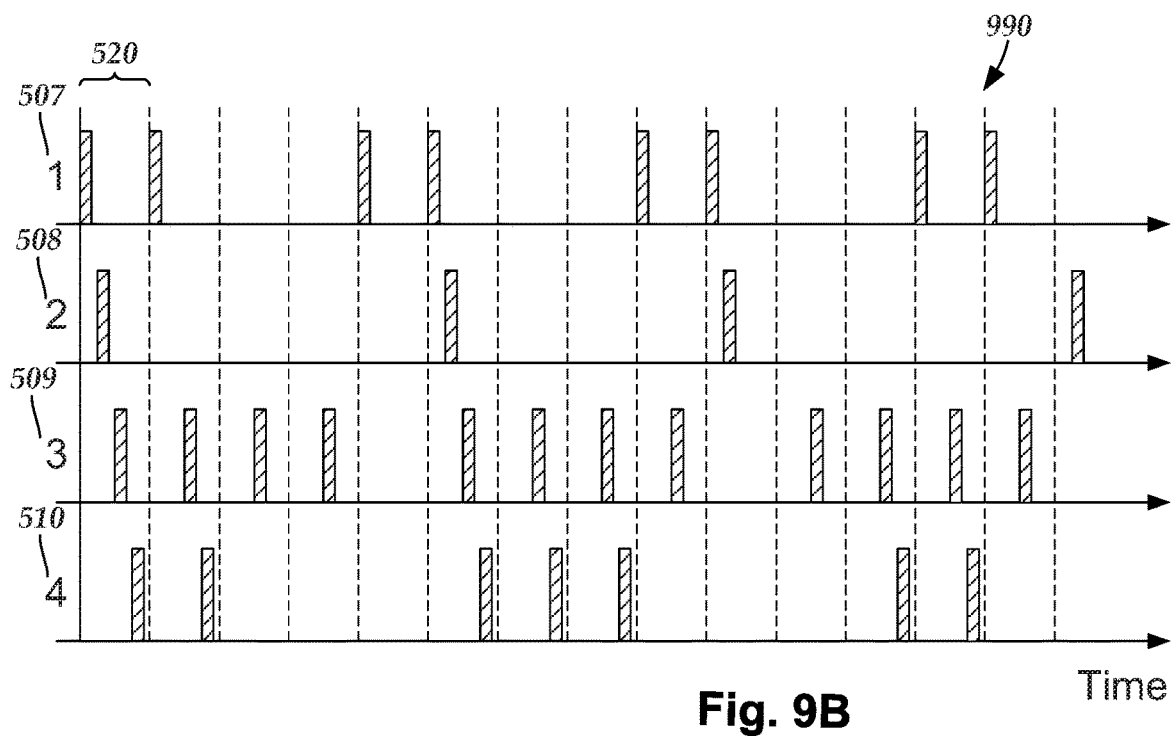
FIG. 9B is a schematic graphical representation of one embodiment of an intermittent stimulation program corresponding to a combination of the repeating arrangements of stimulation instances of FIG. 9A and the ON/OFF-switch pattern of FIG. 9A, according to the invention.

FIG. 9A shows a graphical representation of one embodiment of the repeating arrangements of stimulation instances 520 overlaid onto an ON/OFF-switch pattern 981 with multiple sub-patterns 981a-d. FIG. 9B shows a graphical representation of one embodiment of an intermittent stimulation program 990 corresponding to a combination of the ON/OFF-switch pattern 981 and the repeating arrangements of stimulation instances 520.

The multiple ON/OFF-switch sub-patterns 981a-d can include any suitable combinations of ON/OFF-switch periods, such as any combination utilizing one or more of the above-described ON/OFF-switch periods. In at least some embodiments, at least one of the multiple ON/OFF-switch sub-patterns includes at least one ON/OFF-switch period with multiple ON periods and OFF periods. In at least some embodiments, at least one of the multiple ON/OFF-switch sub-patterns includes ON and/or OFF periods of uniform duration. In at least some embodiments, at least one of the multiple ON/OFF-switch sub-patterns includes ON and/or OFF periods of non-uniform duration. In at least some embodiments, at least one of the multiple ON/OFF-switch sub-patterns includes at least one ON/OFF-switch pattern with ON and OFF periods of randomly-determined duration.

Any suitable number of different ON/OFF-switch sub-patterns can be utilized. In some embodiments, a different ON/OFF-switch sub-pattern is combined with each recurring stimulation instance. For example, in FIG. 9A ON/OFF-switch sub-pattern 981a is combined with stimulation instance 507, ON/OFF-switch sub-pattern 981b is combined with stimulation instance 508, ON/OFF-switch sub-pattern 981c is combined with stimulation instance 509, and ON/OFF-switch sub-pattern 981d is combined with stimulation instance 510. In other embodiments, at least one of the multiple ON/OFF-switch sub-patterns is combined with at least two of the recurring stimulation instances. In other embodiments, at least one of the multiple ON/OFF-switch sub-patterns is combined with at least three of the recurring stimulation instances. In at least some embodiments, at least two different ON/OFF-switch sub-patterns are concurrently combined with at least one stimulation instance.

Figure 10A:
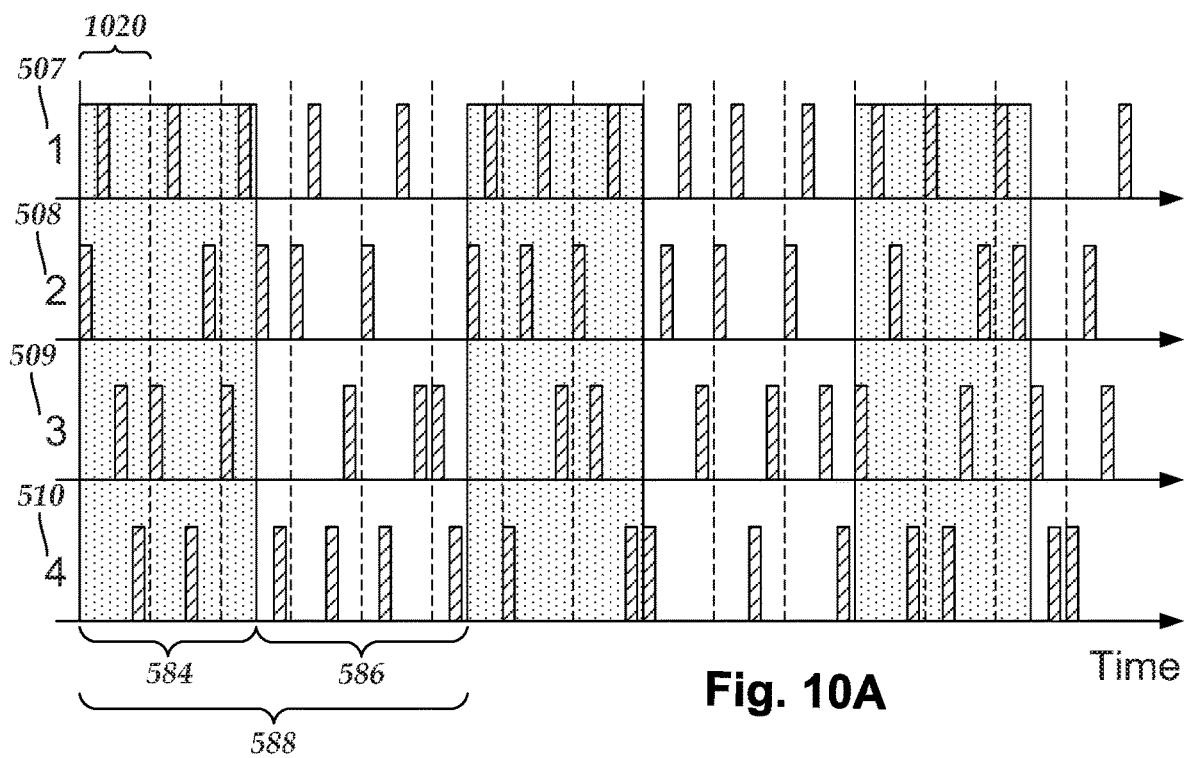
FIG. 10A is a schematic graphical representation of another embodiment of repeating arrangements of stimulation instances and the ON/OFF-switch pattern of FIG. 5C, the repeating arrangements of stimulation instances including stimulation instances occurring sequentially in a randomly-determined order during each arrangement, according to the invention.

Turning to FIG. 10A, in the previously-described embodiments the ordering of the recurring stimulation instances within the arrangements is constant. In other words, in the previously-described embodiments the different recurring stimulation instances (e.g., stimulation instances 507-510) occur in a predetermined order in time. In some embodiments, the ordering of the recurring stimulation instances within the repeated arrangements of stimulation instances are non-uniform. In some embodiments, the recurring stimulation instances within the repeated arrangements are randomly determined, or deterministically determined.

The ordering of the stimulation instances can be determined using any suitable technique. For example, in at least some embodiments each stimulation instance within each arrangement is randomly determined. In other embodiments, the ordering of each of the stimulation instances within a given arrangement of stimulation instances can be randomly determined at once. In yet other embodiments, the ordering of the stimulation instances for multiple arrangements of stimulation instances can be randomly determined at once. Other techniques for randomly determining the ordering of stimulation instances are possible. In some embodiments, multiple techniques are utilized. In at least some embodiments, regardless of the ordering of the stimulation instances within the arrangements of stimulation instances, each recurring stimulation instance occurs exactly once during each arrangement.

In at least some embodiments, the ordering of the recurring stimulation instances within the arrangements of stimulation instances is randomly determined at regular time intervals (e.g., every 10 milliseconds, 50 milliseconds, 100 milliseconds, 500 milliseconds, 1 second, 2 seconds, 3 seconds, 5 seconds, or longer). In at least some embodiments, the ordering of the recurring stimulation instances within the arrangements of stimulation instances is randomly determined at least once during each arrangement.

Figure 10B:
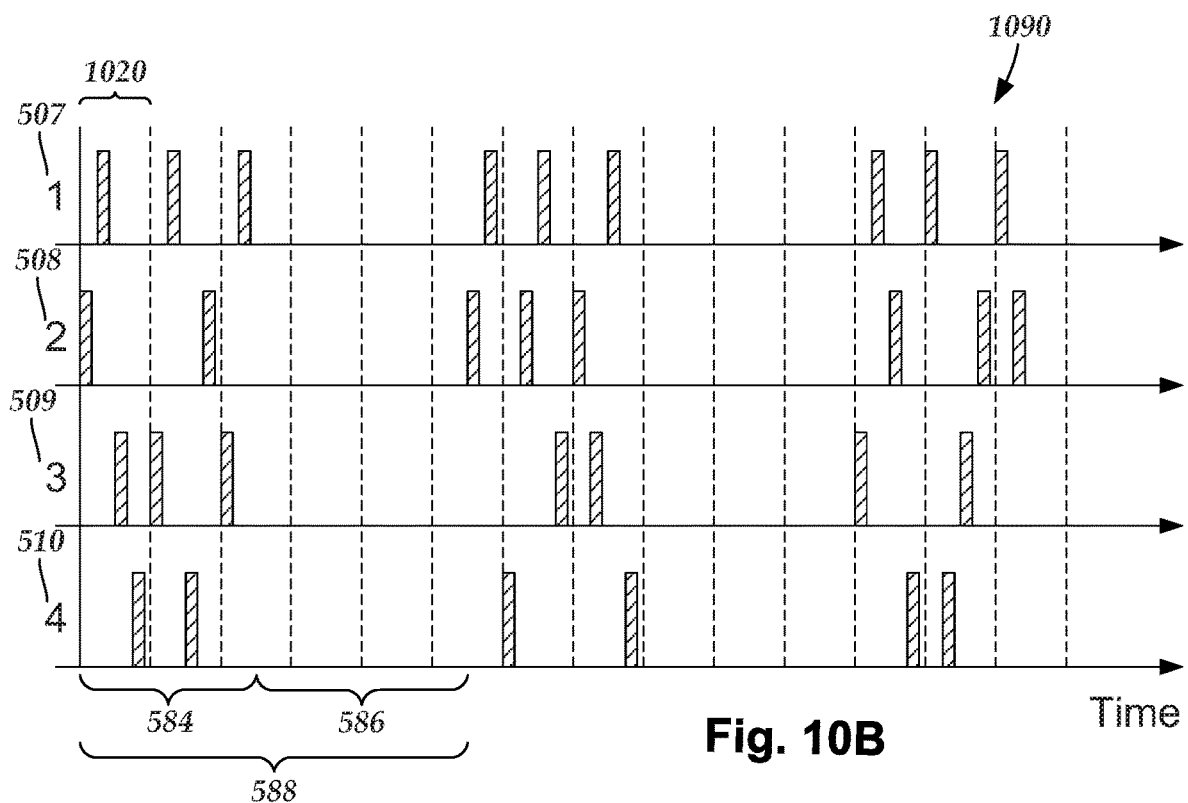
FIG. 10B is a schematic graphical representation of one embodiment of an intermittent stimulation program corresponding to a combination of the repeating arrangements of stimulation instances of FIG. 10A and the ON/OFF-switch pattern of FIG. 10A, according to the invention.

FIG. 10A shows a graphical representation of one embodiment of repeating arrangements of stimulation instances, such as arrangement 1020, overlaid onto the ON/OFF-switch pattern 581, where the ordering of the stimulation instances within each of the arrangements 1020 is randomly determined. FIG. 10B shows a graphical representation of one embodiment of an intermittent stimulation program 1090 corresponding to a combination of the ON/OFF-switch pattern 581 and the repeating arrangements 1020.

The repeating arrangements of stimulation instances each include recurring stimulation instances 507-510. In FIGS. 10A-10B, each of the four stimulation instances occurs exactly once during each arrangement 1020. The ordering of the stimulation instances within each arrangement is randomly determined. Vertical dashed lines depict boundaries between adjacent arrangements 1020. The ON/OFF-switch pattern 581 is shown alternating between ON periods 584 and OFF periods 586 according to a regular schedule of repeating ON/OFF-switch periods, such as ON/OFF-switch period 588.

In embodiments implementing repeating arrangements of randomly-ordered stimulation instances, the arrangements can be combined with any suitable ON/OFF-switch pattern. In FIGS. 10A-10B, the ON/OFF-switch pattern 581 is shown alternating between an ON period 584 and an OFF period 586 according to a regular schedule of repeating ON/OFF-switch periods 588. In at least some embodiments, multiple ON/OFF-switch patterns are combined with different subsets of the recurring stimulation instances. In at least some embodiments, the ON/OFF-switch pattern includes an ON/OFF-switch period with multiple ON and OFF periods. In at least some embodiments, the ON/OFF-switch pattern randomly alternates between ON and OFF periods.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

The above specification and examples provide a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. A system for providing electrical stimulation to a patient, the system comprising:
a processor configured to:
provide, for a plurality of channels for stimulation, a time-ordered arrangement of a plurality of stimulation instances arising from all of the channels that produce stimulation instances, wherein each of the stimulation instances in the arrangement has a corresponding set of stimulation parameters, including a stimulation duration, and is configured to produce a different stimulation field from each other stimulation instance in the arrangement;
provide an ON/OFF switch pattern comprising alternating ON periods and OFF periods, wherein at least one of the ON periods or one of the OFF periods is longer than a combined stimulation duration of two consecutive ones of the stimulation instances;
generate an intermittent stimulation program that is a repetition of the arrangement of stimulation instances with omission of each of the stimulation instances of the arrangement occurring during the OFF periods, wherein each repetition of the arrangement of stimulation instances has a same predetermined time duration, wherein a time duration of the ON periods and the OFF periods is selectable from integer and non-integer multiples of the predetermined time duration of each repetition of the arrangement of stimulation instances; and initiate a signal that provides a pulse generator with instructions that enable the pulse generator to generate stimulation according to the intermittent stimulation program using an electrical stimulation lead coupled to the pulse generator.

2. The system of claim 1, further comprising:

a pulse generator in communication with the processor, the pulse generator configured and arranged to generate stimulation according to the intermittent stimulation program; and an electrical stimulation lead coupleable to the pulse generator, the electrical stimulation lead comprising a plurality of electrodes configured and arranged to stimulate patient tissue when coupled to the pulse generator.

3. The system of claim 2, wherein the set of stimulation parameters for each stimulation instance of the intermittent stimulation program comprises a selection of an individual electrode or a subset of electrodes from the plurality of electrodes.

4. The system of claim 1, wherein the predetermined time duration corresponds to a period of a frequency within a pathological frequency range associated with a neuronal population at a target stimulation location.

5. The system of claim 1, wherein the ON periods of the ON/OFF-switch pattern have equal duration to the OFF periods.

6. The system of claim 1, wherein each of the stimulation instances occurs exactly once in the arrangement and in a predetermined order in time.

7. The system of claim 1, wherein the ON periods of the ON/OFF-switch pattern are of uniform duration.

8. The system of claim 1, wherein the ON periods of the ON/OFF-switch pattern are of non-uniform duration.

9. The system of claim 1, wherein the OFF periods of the ON/OFF-switch pattern are of uniform duration.

10. The system of claim 1, wherein the OFF periods of the ON/OFF-switch pattern are of non-uniform duration.

11. The system of claim 1 wherein the ON periods and the OFF periods of the ON/OFF-switch pattern are of randomly-determined durations.

12. A method for providing intermittent electrical stimulation to a patient, the method comprising:

advancing an electrical stimulation lead to a target stimulation location within the patient, the electrical stimulation lead comprising a plurality of electrodes;

coupling the electrical stimulation lead to a pulse generator configured and arranged for providing electrical stimulation signals to the plurality of electrodes for stimulation of patient tissue; and using the system of claim 1 for initiating signals that provide the pulse generator with instructions that enable the pulse generator to generate stimulation according to the intermittent pattern of stimulations of the system using the electrical stimulation lead.

13. The method of claim 12, further comprising programming the repeating arrangements of stimulation instances of the system to have a time duration that corresponds in length to a period corresponding to a pathological frequency range associated with a neuronal population at a target stimulation location in proximity to the plurality of electrodes.

14. A non-transitory computer-readable medium having processor-executable instructions for programming electrical stimulation by an electrical stimulation lead, the processor-executable instructions when installed onto a device enable the device to perform actions comprising:

providing, for a plurality of channels for stimulation, a time-ordered arrangement of a plurality of stimulation instances arising from all of the channels that produce stimulation instances, wherein each of the stimulation instances in the arrangement has a corresponding set of stimulation parameters, including a stimulation duration, and is configured to produce a different stimulation field from each other stimulation instance in the arrangement;

providing an ON/OFF switch pattern comprising alternating ON periods and OFF periods, wherein at least one of the ON periods or one of the OFF periods is longer than a combined stimulation duration of two consecutive ones of the stimulation instances;

generating an intermittent stimulation program that is a repetition of the arrangement of stimulation instances with omission of each of the stimulation instances of the arrangement occurring during the OFF periods, wherein each repetition of the arrangement of stimulation instances has a same predetermined time duration, wherein a time duration of the ON periods and the OFF periods is selectable from integer and non-integer multiples of the predetermined time duration of each repetition of the arrangement of stimulation instances; and initiating a signal that provides a pulse generator with instructions that enable the pulse generator to generate stimulation according to the intermittent stimulation program using an electrical stimulation lead coupled to the pulse generator.

15. A system for providing electrical stimulation to a patient, the system comprising:

a processor configured to:

provide, for a plurality of channels for stimulation, a time-ordered arrangement of a plurality of stimulation instances arising from all of the channels that produce stimulation instances, wherein each of the stimulation instances in the arrangement has a corresponding set of stimulation parameters, including a stimulation duration, and is configured to produce a different stimulation field from each other stimulation instance in the arrangement, wherein each of the stimulation instances occurs in a non-uniform order in time;

provide an ON/OFF switch pattern comprising alternating ON periods and OFF periods, wherein at least one of the ON periods or one of the OFF periods is longer than a combined stimulation duration of two consecutive ones of the stimulation instances;

generate an intermittent stimulation program that is a repetition of the arrangement of stimulation instances with omission of each of the stimulation instances of the arrangement occurring during the OFF periods, wherein each repetition of the arrangement of stimulation instances has a same predetermined time duration, wherein a time duration of the ON periods and the OFF periods is selectable from integer and non-integer multiples of the predetermined time duration of each repetition of the arrangement of stimulation instances; and initiate a signal that provides a pulse generator with instructions that enable the pulse generator to generate stimulation according to the intermittent stimulation program using an electrical stimulation lead coupled to the pulse generator.

16. The system of claim 15, wherein each of the stimulation instances occurs exactly once in the arrangement and in a randomly-determined order in time.

17. A method for providing intermittent electrical stimulation to a patient, the method comprising:
- advancing an electrical stimulation lead to a target stimulation location within the patient, the electrical stimulation lead comprising a plurality of electrodes;
- coupling the electrical stimulation lead to a pulse generator configured and arranged for providing electrical stimulation signals to the plurality of electrodes for stimulation of patient tissue; and
- using the system of claim 15 for initiating signals that provide the pulse generator with instructions that enable the pulse generator to generate stimulation according to the intermittent pattern of stimulations of the system using the electrical stimulation lead.

18. The method of claim 17, wherein the predetermined time duration corresponds in length to a period corresponding to a pathological frequency range associated with a neuronal population at the target stimulation location.

* * * * *